(12) United States Patent
Liu et al.

(10) Patent No.: US 8,106,209 B2
(45) Date of Patent: *Jan. 31, 2012

(54) SUBSTITUTED AMINOTHIAZOLE PRODRUGS OF COMPOUNDS WITH ANTI-HCV ACTIVITY

(75) Inventors: Cuixan Liu, Madison, CT (US);
Avinash Phadke, Branford, CT (US);
Xiangzhu Wang, Branford, CT (US);
Suoming Zhang, Palo Alto, CA (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/479,213

(22) Filed: Jun. 5, 2009

(65) Prior Publication Data
US 2009/0304605 A1   Dec. 10, 2009

Related U.S. Application Data

(60) Provisional application No. 61/059,383, filed on Jun. 6, 2008.

(51) Int. Cl.
C07D 417/04 (2006.01)
A61K 31/44 (2006.01)

(52) U.S. Cl. .................................. 546/270.4; 514/342

(58) Field of Classification Search ............... 546/270.4; 514/342
See application file for complete search history.

(56) References Cited

U.S. PATENT DOCUMENTS

| | | | |
|---|---|---|---|
| 3,467,666 A | 9/1969 | Dexter et al. | |
| 5,856,347 A | 1/1999 | Hashiguchi et al. | |
| 7,115,746 B2 | 10/2006 | Snoonian et al. | |
| 7,163,952 B2 | 1/2007 | Inaba et al. | |
| 7,169,931 B2 | 1/2007 | Takemoto et al. | |
| 7,232,838 B2 | 6/2007 | Love et al. | |
| 2002/0016471 A1 | 2/2002 | Salituro et al. | |
| 2004/0186148 A1 | 9/2004 | Shankar et al. | |
| 2007/0004711 A1* | 1/2007 | Zhang et al. | 514/227.5 |
| 2007/0213301 A1* | 9/2007 | Zhang et al. | 514/92 |
| 2008/0004279 A1 | 1/2008 | Moussy et al. | |
| 2009/0041720 A1* | 2/2009 | Wang et al. | 424/85.4 |

FOREIGN PATENT DOCUMENTS

| | | |
|---|---|---|
| EP | 0154190 A1 | 8/1985 |
| EP | 0790057 B1 | 5/2002 |
| EP | 1321463 A | 6/2003 |
| EP | 1354603 A1 | 10/2003 |
| EP | 1599468 B1 | 3/2007 |
| EP | 1525200 B1 | 10/2007 |
| WO | 0006575 A2 | 2/2000 |
| WO | 0121160 A2 | 3/2001 |
| WO | 0153267 A1 | 7/2001 |
| WO | 03028729 A2 | 4/2003 |
| WO | 03062215 A1 | 7/2003 |
| WO | 2004071447 A2 | 8/2004 |
| WO | 2004076693 A1 | 9/2004 |
| WO | 2004085385 A2 | 10/2004 |
| WO | 2004092145 A1 | 10/2004 |
| WO | 2005007647 A1 | 1/2005 |

(Continued)

OTHER PUBLICATIONS

Riley, Thomas, "The Prodrug Concept and New Drug Design and Development", Journal of Chemical Education, vol. 65, No. 11, Nov. 1988, pp. 947-953.*

(Continued)

*Primary Examiner* — Janet Andres
*Assistant Examiner* — Heidi Reese
(74) *Attorney, Agent, or Firm* — Cantor Colburn LLP

(57) ABSTRACT

The invention provides amino-substituted aminothiazole compounds of Formula I and Formula II

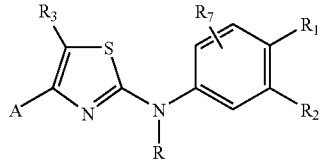
(Formula II-A)

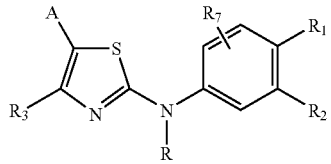

(Formula II-B)

where A is a group of the formula:

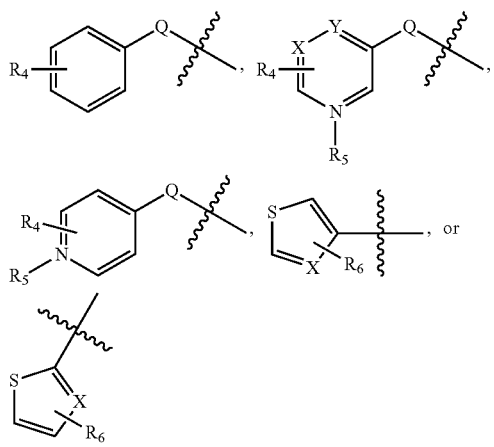

and the variables X, Y, R, and $R_1$ to $R_7$ are described herein. These compounds are prodrugs of compounds useful as inhibitors of viral replication. Compositions containing such compounds, and methods of treating viral infections with these compounds, as well as to processes and intermediates useful for preparing such compounds are also provided by the invention.

19 Claims, No Drawings

FOREIGN PATENT DOCUMENTS

| | | | |
|---|---|---|---|
| WO | 2005016323 | A2 | 2/2005 |
| WO | 2005073225 | A1 | 8/2005 |
| WO | 2005077368 | A2 | 8/2005 |
| WO | 2005082089 | A2 | 9/2005 |
| WO | 2005099673 | A1 | 10/2005 |
| WO | 2005102318 | A1 | 11/2005 |
| WO | 2005102325 | A1 | 11/2005 |
| WO | 2005102326 | A2 | 11/2005 |
| WO | 2005102346 | A2 | 11/2005 |
| WO | 2005102455 | A1 | 11/2005 |
| WO | 2005112920 | A1 | 12/2005 |
| WO | 2005115304 | A2 | 12/2005 |
| WO | 2005115385 | A1 | 12/2005 |
| WO | 2006028029 | A1 | 3/2006 |
| WO | 2006033005 | A2 | 3/2006 |
| WO | 2006113261 | A2 | 10/2006 |
| WO | 2006122011 | A2 | 11/2006 |
| WO | 2006122250 | A2 | 11/2006 |
| WO | 2007026251 | A2 | 3/2007 |
| WO | 2007065939 | A1 | 6/2007 |
| WO | 2007088996 | A1 | 8/2007 |
| WO | 2007089743 | A2 | 8/2007 |
| WO | 2007095603 | A2 | 8/2007 |
| WO | 2007103550 | A2 | 9/2007 |
| WO | 2008033932 | A2 | 3/2008 |
| WO | 2008106202 | A1 | 9/2008 |
| WO | 2008145616 | A1 | 12/2008 |

OTHER PUBLICATIONS

Kuleshova, L.N. et al., "Conformational Polymorphism of N-(4-Butoxyphenyl)-4-(4'-Nitrophenyl)-2-Thiazolamine," Crystallography Reports, (2003) 49(5): 798-806.

Shipps, G.W., et al., "Aminothiazole inhibitors of HCV RNA polymerase," Bioorganic & Med. Chem. Lett. 15: 115-119 (2005).

Moyer, et al., "Hepatitis C: Part II Prevention Counseling and Medical Evaluation," American Family Physician 59(2): 349-354 (1999).

Parvate, J.A. "Synthesis of substituted 4,2'-bis thiazoles," Indian Drugs, 26(5): 222-226 (1989).

Truce, W.E., et al. "The Stereochemistry of the Reaction of Tetrachloroethylene with p-toluene-thiolate reagent," Tetrahedron 21: 2899-2905 (1965).

International Search Report for PCT US2006/017692, 2006.
Written Opinion for US 2006/017692, 2006.
International Search Report for PCT US08/006676, 2008.
Written Opinion for PCT US08/006676, 2008.
International Search Report for PCT/US2007/006023, 2007.
Written Opinion for PCT/US2007/006023, 2007.
International Search Report for PCT/US2009/046549, 2009.
Written Opinion for PCT/US2009/046549, 2009.
Patentability Report for International Application No. PCT/US2009/046549 dated Dec. 16, 2010.

* cited by examiner

SUBSTITUTED AMINOTHIAZOLE PRODRUGS OF COMPOUNDS WITH ANTI-HCV ACTIVITY

CROSS REFERENCE TO RELATED APPLICATIONS

This application claims priority from U.S. Provisional Patent application No. 61/059,383, filed Jun. 6, 2008, which is hereby incorporated by reference in its entirety.

FIELD OF THE INVENTION

The present invention provides substituted aminothiazole prodrugs of compounds with Anti-HCV Activity. The invention also includes methods for preparing such compounds. The present invention further includes pharmaceutical compositions containing substituted aminothiazole prodrug compounds and methods for using such compounds, including methods for using the prodrug compounds to treat hepatitis C infection.

BACKGROUND

An estimated 3% of the world's population is infected with the hepatitis C virus. Of those exposed to HCV, 80% become chronically infected, at least 30% develop cirrhosis of the liver and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will clear HCV.

HCV is an enveloped, single-stranded RNA virus that contains a positive-stranded genome of about 9.6 kb. HCV is classified as a member of the Hepacivirus genus of the family Flaviviridae. At least 4 strains of HCV, GT-1-GT-4, have been characterized.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is:

NH2-C-E1-E2-p7-NS2-NS3-NS4A-NS4B—NS5A-NS5B—COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B-NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at three downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus. Assembly of a functional replicase complex has been described as a component of the HCV replication mechanism. Provisional application 60/669,872 "Pharmaceutical Compositions and Methods of Inhibiting HCV Replication" filed Apr. 11, 2005, is hereby incorporated by reference in its entirety for its disclosure related to assembly of the replicase complex.

Current treatment of hepatitis C infection typically includes administration of an interferon, such as pegylated interferon (IFN), in combination with ribavirin. The success of current therapies as measured by sustained virologic response (SVR) depends on the strain of HCV with which the patient is infected and the patient's adherence to the treatment regimen. Only 50% of patients infected with HCV strain GT-1 exhibit a sustained virological response. Direct acting antiviral agents such as ACH-806, VX-950 and NM 283 (prodrug of NM 107) are in clinical development for treatment of chronic HCV.

Due to lack of effective therapies for treatment for certain HCV strains and the high mutation rate of HCV, new therapies are needed. The present invention fulfills this need and provides additional advantages, which are described herein.

SUMMARY OF THE INVENTION

The present invention generally relates to methods for inhibiting HCV, and compounds useful in such methods.

In another aspect the invention provides prodrug compounds of Formula IA and IB and pharmaceutically acceptable salts thereof:

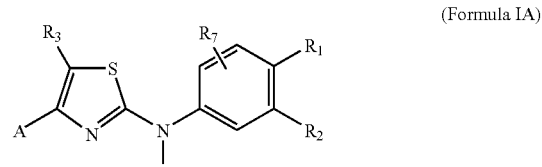

(Formula IA)

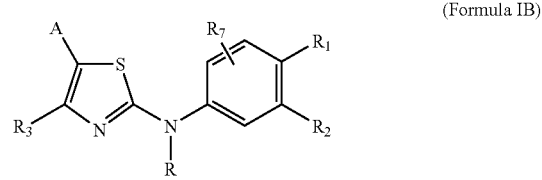

(Formula IB)

Within Formula IA and IB, A is a group of the formula:

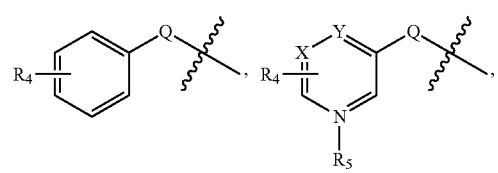

-continued

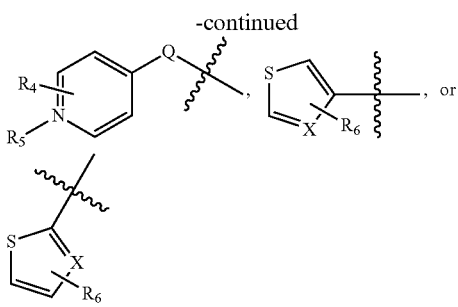

Q is O, S, N, CH$_2$, or absent.

X is N or CH; Y is N or CH; and not more that one of X and Y is N.

R$_1$ and R$_2$ are L and M, where one of R$_1$ and R$_2$ is L and the other is M, and where L is hydrogen, halogen, hydroxyl, amino, cyano, —COOH, —CONH$_2$, C$_1$-C$_4$alkyl, C$_1$-C$_4$alkoxy, C$_2$-C$_4$alkanoyl, C$_1$-C$_2$alkylester, C$_1$-C$_2$alkylsulfonyl, C$_1$-C$_2$haloalkyl, or C$_1$-C$_2$haloalkoxy.

M is C$_2$-C$_{20}$carbohydryl, C$_2$-C$_{20}$carbohydryloxy, C$_2$-C$_{20}$alkanoyl, or mono- or di-C$_2$-C$_{20}$alkylamino, each of which M may contain one or more oxygen atoms, nitrogen atoms, sulfur atoms, or sulfonyl groups and is substituted with 0 or 1 or more substituents independently chosen from halogen, hydroxyl, cyano, amino, C$_1$-C$_2$haloalkyl, C$_1$-C$_2$haloalkoxy, and oxo, and may also be substituted with one aryl, mono- or bicyclic heteroaryl, C$_3$-C$_7$cycloalkyl, or 5- to 7-membered heterocycloalkyl, or M is a mono- or bi-cyclic carbocyclic group, a mono- or bi-cyclic carbocycloxy, a 5- or 6-membered heteroaryl group, containing 0, 1, or 2 heteroatoms chosen from N, O, and S, or a 5- or 6-membered heteroaryloxy, containing 0, 1, or 2 heteroatoms chosen from N, O, and S; each of which is carbocyclic group, carbocycloxy, heteroaryl group, or heteroaryloxy is substituted with 0 or 1 or more substituents independently chosen from halogen, hydroxyl, cyano, C$_1$-C$_4$alkyl, C$_1$-C$_4$alkoxy, C$_2$-C$_4$alkanoyl, mono- and di-C$_1$-C$_4$alkylamino, C$_1$-C$_2$haloalkyl, and C$_1$-C$_2$haloalkoxy.

Or, R$_1$ and R$_2$ are taken together to form a 5- or 6-membered carbocyclic or heterocyclic ring, which is saturated, partially unsaturated, or aromatic, and is substituted with 0, 1, or 2 substituents independently chosen from halogen, hydroxyl, amino, cyano, C$_1$-C$_{10}$alkyl, C$_2$-C$_{10}$alkenyl, C$_1$-C$_{10}$alkoxy, and optionally substituted (phenyl)C$_0$-C$_4$alkyl.

R$_3$ is hydrogen, halogen, hydroxyl, amino, cyano, C$_1$-C$_2$alkyl, or (mono- or di-C$_1$-C$_2$alkylamino)C$_0$-C$_2$alkyl.

R$_4$ represents 0 or 1 or more substituents independently chosen from (a) and (b) and 0 or 1 substituents chosen from (c):
(a) halogen, hydroxyl, amino, cyano, —COOH, —CONH$_2$, —PO$_4$, C$_1$-C$_2$haloalkyl, and C$_1$-C$_2$haloalkoxy;
(b) C$_1$-C$_4$alkyl and C$_1$-C$_4$alkoxy, each of which is substituted with 0 or 1 or more substituents independently chosen from halogen, hydroxyl, amino, cyano, oxo, C$_1$-C$_2$alkyl, C$_1$-C$_2$alkoxy, and mono- and di-C$_1$-C$_2$alkylamino;
(c) mono- and di-C$_1$-C$_4$alkylamino, mono- and di-C$_1$-C$_4$alkylcarboxamide, C$_2$-C$_4$alkanoyl, mono- and di-C$_1$-C$_4$alkylphosphate, C$_1$-C$_4$aminoalkyl, C$_1$-C$_4$aminoalkoxy, C$_1$-C$_4$hydroxyalkyl, C$_1$-C$_4$alkylester, (C$_3$-C$_7$cycloalkyl)C$_0$-C$_2$alkyl, or (5- or 6-membered heterocycloalkyl)C$_0$-C$_2$alkyl, each of which is substituted with 0 or 1 or more substituents independently chosen from halogen, hydroxyl, amino, cyano, oxo, C$_1$-C$_2$alkyl, C$_1$-C$_2$alkoxy, and mono- and di-C$_1$-C$_2$alkylamino.

Any two R$_4$ groups, covalently bound to adjacent atoms, may be joined to form a 5-membered heterocyclic group containing 1 or 2 additional heteroatoms independently chosen from N, O, and S, wherein the 5- or 6-membered heterocyclic group is optionally substituted.

R$_5$ is absent, oxygen, or C$_1$-C$_4$alkyl.

R$_6$ is 0 or 1 or more substituents independently chosen from
(i) hydroxyl, halogen, amino, cyano, —COOH, —CONH$_2$, —PO$_4$, C$_1$-C$_2$haloalkyl, and C$_1$-C$_2$haloalkoxy;
(ii) C$_1$-C$_4$alkyl, C$_1$-C$_4$alkoxy, mono- and di-C$_1$-C$_4$alkylamino, C$_2$-C$_4$alkanoyl, C$_1$-C$_4$alkylphosphate, and C$_1$-C$_4$alkylester, each of which is substituted with 0 or 1 or more substituents independently chosen from halogen, hydroxyl, amino, cyano, C$_1$-C$_2$alkoxy, mono- and di-C$_1$-C$_2$alkylamino.

R$_7$ is 0 or 1 or more substituents independently chosen from halogen, hydroxyl, amino, cyano, C$_1$-C$_2$alkyl, C$_1$-C$_2$alkoxy, C$_1$-C$_2$haloalkyl, and C$_1$-C$_2$haloalkoxy.

R is a group of the formula:

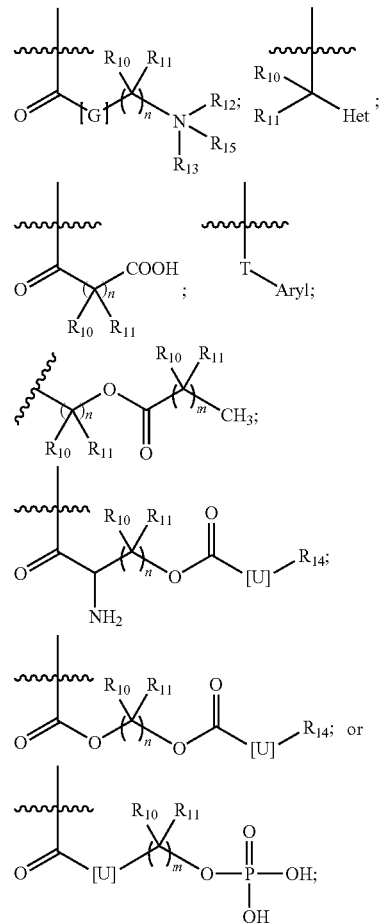

R$_{10}$ and R$_{11}$ are independently chosen at each occurrence from hydrogen, amino, C$_1$-C$_4$alkyl, C$_1$-C$_4$aminoalkyl, and C$_1$-C$_4$hydroxyalkyl.

$R_{12}$ and $R_{13}$ are independently chosen from hydrogen and $C_1$-$C_4$alkyl. $R_{14}$ is hydrogen, or $R_{14}$ is hydroxyl or —COOH; or $R_{14}$ is $C_1$-$C_4$alkyl substituted with 0 to 3 halogen and 0 or 1 substituents chosen from —COOH, —OPO(OH)$_2$, amino, hydroxyl, mono- and di-$C_1$-$C_4$alkylamino, mono- and di-$C_1$-$C_2$alkylcarboxamide, and mono- or di-$C_1$-$C_2$alkylester, or $R_{14}$ is ($C_3$-$C_6$cycloalkyl)$C_1$-$C_2$alkyl, substituted with 0 to 3 halogen atoms and substituted with 0 or 1 substituent chosen from hydroxyl, —COOH, amino, and —NHBoc. Or, $R_{14}$ is absent and [U] is phenyl or pyridyl;

$R_{15}$ is absent; hydrogen or $C_1$-$C_2$alkyl.

The variable "n" is an integer from 1 to 4, independently chosen at each occurrence.

The variable "m" is an integer from 0 to 4, independently chosen at each occurrence.

[G] is oxygen or absent.

T is O or S.

Aryl is phenyl or pyridyl; each of which is substituted with 0 to 3 substituents independently chosen from halogen, hydroxyl, amino, cyano, oxo, $C_1$-$C_2$alkyl, $C_1$-$C_2$alkoxy, $C_1$-$C_2$mono- and di-alkylamino.

Het is a 5- to 6-membered heteroaryl or unsaturated heterocylic group containing 1 to 4 heteroatoms independently chosen from O, S, and N, remaining ring atoms are carbon, and Het is substituted with 0 to 3 substituents independently chosen from halogen, hydroxyl, amino, cyano, oxo, $C_1$-$C_2$alkyl, $C_1$-$C_2$alkoxy, and mono- and di-$C_1$-$C_2$alkylamino.

[U] is absent or is phenyl, pyridyl, thienyl, $C_3$-$C_7$cycloalkyl, 5- or 6-membered heterocycloalkyl containing 1 nitrogen atom and 0 or 1 additional heteroatoms chosen from O, S, and N, or 5- to 6-membered heteroaryl containing 1 to 4 heteroatoms independently chosen from O, S, and N, remaining ring atoms are carbon; where each [U] group is substituted with 0 to 3 groups independently chosen from halogen, hydroxyl, amino, cyano, $C_1$-$C_2$alkyl, $C_1$-$C_2$alkoxy, and mono- and di-$C_1$-$C_2$alkylamino.

Wherein the compound of Formula IA or IB is not 2-amino-N-(5-fluoro-4-(pyridin-3-yl)thiazol-2-yl)-3-methyl-N-(4-octyl-3-(trifluoromethyl)phenyl)butanamide; 2-(4-((5-fluoro-4-(pyridin-3-yl)thiazol-2-yl)(4-octyl-3-(trifluoromethyl)phenyl)amino)-2-methyl-4-oxobutan-2-yl)-3,5-dimethylphenyl dihydrogen phosphate; 2-(phosphonooxy)ethyl-5-fluoro-4-(pyridin-3-yl)thiazol-2-yl(4-octyl-3-(trifluoromethyl)phenyl)carbamate; 2-((5-fluoro-4-(pyridin-3-yl)thiazol-2-yl)(4-octyl-3-(trifluoromethyl)phenyl)amino)-2-oxoethyl dihydrogen phosphate; 4-((5-fluoro-4-(pyridin-3-yl)thiazol-2-yl)(4-octyl-3-(trifluoromethyl)phenyl)amino)-4-oxobutyl dihydrogen phosphate; ((5-fluoro-4-(pyridin-3-yl)thiazol-2-yl)(4-octyl-3-(trifluoromethyl)phenyl)carbamoyl-oxy)methyl 2-amino-3-methylbutanoate; or phosphonooxymethyl 5-fluoro-4-(pyridin-3-yl)thiazol-2-yl(4-octyl-3-(trifluoromethyl)phenyl)carbamate.

The invention includes pharmaceutical compositions comprising a compound of the invention or a salt thereof, containing at least one pharmaceutically acceptable carrier. The invention also includes pharmaceutical compositions comprising a compound of the invention and containing at least one additional active agent. The invention includes methods of treatment comprising providing a patient with a compound of the invention together with together with instructions for using the compound to treat and/or prevent HCV infection in the patient.

In another aspect the invention provides a method for treating or preventing hepatitis C infection comprising providing an effective amount of a compound or salt of the invention to a patient in need of such treatment or prevention.

A method of inhibiting HCV replication in vivo comprising administering to a patient infected with HCV a concentration of a compound or salt of the invention sufficient to inhibit HCV replicon replication in vitro is also included in the invention. Methods of inhibiting HCV activity that comprise treating a sample containing HCV with an HCV inhibitory amount of at least one compound of Formula IA or IB are included. The sample may be a cell or tissue sample, and may be present in vitro or in a patient.

These and other aspects of the invention will be more clearly understood with reference to the following detailed description, examples and claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

I. Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs.

Formula I includes all compounds of Formula IA and IB and all subformulae thereof.

When tradenames are used herein, applicants intend to independently include the tradename product and the active pharmaceutical ingredient(s) of the tradename product.

The terms "a" and "an" do not denote a limitation of quantity, but rather denote the presence of at least one of the referenced items. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound of the invention), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of an active agent may be employed either alone or in combination.

In certain situations, the compounds of the invention may contain one or more asymmetric elements such as stereogenic centers, including chiral centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. Formula I include all chiral forms, stereoisomers, diastereomers, and enantiomers of compounds of Formula I.

The term "chiral" refers to molecules, which have the property of non-superimposability of the mirror image partner.

"Stereoisomers" are compounds, which have identical chemical constitution, but differ with regard to the arrangement of the atoms or groups in space.

A "Diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Where a compound exists in various tautomeric forms, the invention is not limited to any one of the specific tautomers, but rather includes all tautomeric forms.

The invention includes compounds of the invention having all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. A, R, and $R_1$ to $R_3$. Unless otherwise specified, each variable within the invention is defined independently of other variables. Thus, if a group is said to be substituted, e.g. with 0-2 R*, then said group may be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —($CH_2$)$C_3$-$C_7$cycloalkyl is attached through carbon of the methylene ($CH_2$) group.

"Alkyl" includes both branched and straight chain saturated aliphatic hydrocarbon groups, having the specified number of carbon atoms, generally from 1 to about 18 carbon atoms, or more preferably from 1 to about 12 carbon atoms. The term $C_1$-$C_6$alkyl as used herein indicates an alkyl group having from 1 to about 6 carbon atoms. When $C_0$-$C_n$ alkyl is used herein in conjunction with another group, for example, (phenyl)$C_0$-$C_4$ alkyl, the indicated group, in this case phenyl, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkanoyl" is an alkyl group as defined above, attached through a keto (—(C═O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

"Alkenyl" means straight and branched hydrocarbon chains comprising one or more unsaturated carbon-carbon bonds, which may occur in any stable point along the chain. Alkenyl groups described herein typically have from 2 to about 12 carbons atoms. Preferred alkenyl groups are lower alkenyl groups, those alkenyl groups having from 2 to about 8 carbon atoms, e.g. $C_2$-$C_8$, $C_2$-$C_6$, and $C_2$-$C_4$ alkenyl groups. Examples of alkenyl groups include ethenyl, propenyl, and butenyl groups.

"Alkoxy" means an alkyl group, as defined above, with the indicated number of carbon atoms attached via an oxygen bridge. Examples of alkoxy include, but are not limited to, methoxy, ethoxy, 3-hexoxy, and 3-methylpentoxy. When $C_0$-$C_n$ alkoxy is used herein in conjunction with another group, for example, (heterocycloalkyl)$C_0$-$C_2$alkoxy, the indicated group, in this case heterocycloalkyl, is either bound through and oxygen linker, i.e. heterocycloalkyl-O—, ($C_0$alkoxy), or bound via the oxygen group of an alkoxy chain having the specified number of carbon atoms, in this case from 1 to about 2 carbon atoms.

"Mono- and/or di-alkylamino" indicates secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino. "Mono- and/or dialkylaminoalkyl" groups are mono- and/or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom.

"Aminoalkyl" indicates an alkyl group as described herein substituted with at least one amino substituent. Likewise "hydroxyalkyl" indicates an alkyl group as described herein substituted with at least one —OH substituent.

"Alkylester" indicates an alkyl group as defined above attached through an ester linkage. The ester linkage may be in either orientation, e.g. a group of the formula —O(C═O)alkyl or a group of the formula —(C═O)Oalkyl.

"Alkylphosphate" indicates a phosphoester linkage which is mono- or di-substituted with independently chosen alkyl groups. A mono-alkyl phosphate substituent has the formula alkyl-$HPO_4$— and a di-alkyl phosphate has the formula $alkyl_1 alkyl_2 PO_4$— and the structure

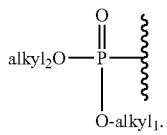

The alkyl groups are as defined above.

"Alkylsulfonyl" is used herein to indicate an alkyl-$SO_2$— group, in which the point of attachment is on the sulfur atom.

"Aryl" means aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

"Mono- and/or di-alkylcarbamate" indicates groups of the formula $(alkyl_1)$-O (C═O)NH— and $(alkyl_1)$-O (C═O)N$(alkyl_2)$- in which the $alkyl_1$ and $alkyl_2$ groups are independently chosen alkyl groups as defined above having the indicated number of carbon atoms.

A "mono- or bicyclic carbocyclic group" is a saturated, unsaturated, or aromatic ring group having only carbon ring atoms. A "mono- or bicyclic carbocycloxy" group is a carbocyclic group attached via an oxygen bridge.

"Carbohydryl" as used herein, includes both branched and straight-chain hydrocarbon groups, which are saturated or unsaturated, having the specified number of carbon atoms. Examples of carbohydryl groups include C1-C6alkyl, such as methyl, or 5-butyl, $C_2$-$C_6$alkynyl such as hexynyl, and $C_2$-$C_6$ alkenyl, such as 1-propenyl.

"Carbohydryloxy" indicates a carbohydryl group, as defined above, attached through an oxygen bridge.

"Mono- and/or di-alkylcarboxamide" indicates groups of formula $(alkyl_1)$-NH—(C═O)— and $(alkyl_1)(alkyl_2)$-N—(C═O)— in which the $alkyl_1$ and $alkyl_2$ groups are independently chosen alkyl groups as defined above having the indicated number of carbon atoms. Mono and/or di-alkylcarboxamide also refers to groups of the formula —NH(C═O)$(alkyl_1)$ and —N$(alkyl_2)$(C═O)$(alkyl_1)$, carboxamide groups in which the point of attachment is the nitrogen atom, in which the $alkyl_1$ and $alkyl_2$ groups are independently chosen alkyl groups as defined above having the indicated number of carbon atoms.

"Cycloalkyl" indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane. In the term "(cycloalkyl)alkyl" the terms "cycloalkyl" and "alkyl" carry the definitions set forth herein and the point of attachment of the (cycloalkyl)alkyl group is in the alkyl linker. Likewise (cycloalkyl)alkoxy indicates a cycloalkyl group covalently bound to the group it substitutes via the oxygen of the linker alkoxy group.

"Heteroaryl" indicates a stable 5- to 7-membered monocyclic aromatic ring which contains from 1 to 3, or in some embodiments from 1 to 2, heteroatoms chosen from N, O, and S, with remaining ring atoms being carbon, or a stable bicyclic system containing at least one 5- to 7-membered aromatic ring which contains from 1 to 3, or in some embodiments from 1 to 2, heteroatoms chosen from N, O, and S, with remaining ring atoms being carbon. "5- or 6-Membered heteroaryl" indicates a stable monocyclic aromatic ring having 5 or 6 ring members and from 1 to 4, or preferably from 1 to 3, ring heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the heteroaryl group is not more than 1. A nitrogen atom in a heteroaryl group may optionally be quaternized. A "heteroaryloxy" is a heteroaryl group attached via an oxygen linker. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, and tetrazolyl.

"Heterocycloalkyl" means a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized. In the term "(heterocycloalkyl)alkyl" the terms "heterocycloalkyl" and "alkyl" carry the definitions set forth herein and the point of attachment of the (heterocycloalkyl)alkyl group is in the alkyl linker.

"Heterocycle" or a "heterocyclic group" indicates saturated, unsaturated, and aromatic ring groups having at least one ring containing a heteroatom chosen from N, O, and S, with remaining ring atoms being carbon.

Examples of heterocycles or heterocyclic groups include by way of example and not limitation pyridyl, dihydroypyridyl, tetrahydropyridyl(piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Haloalkyl" indicates both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge (oxygen of an alcohol radical).

"Halo" or "halogen" as used herein refers to fluoro, chloro, bromo, or iodo.

"Pharmaceutical compositions" are compositions comprising at least one active agent, such as a compound or salt of the invention, and at least one other substance, such as a carrier. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. Any reference to any of the compounds of the invention also includes a reference to a physiologically acceptable salt thereof, unless clearly contraindicated by the context. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions of the invention refers to a diluent, excipient, or vehicle with which an active compound is administered.

A "pharmaceutically acceptable carrier" means an substance, e.g. excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" as used in the present application includes both one and more than one such carrier.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Prodrug" means any compound that becomes compound of the invention when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of the invention.

"Providing" means giving, administering, selling, distributing, transferring (for profit or not), manufacturing, compounding, or dispensing.

"Providing a compound of the invention with at least one additional active agent" means the compound of the invention and the additional active agent(s) are provided simultaneously in a single dosage form, provided concomitantly in separate dosage forms, or provided in separate dosage forms for administration separated by some amount of time that is within the time in which both the compound of the invention and the at least one additional active agent are within the blood stream of a patient. The compound of the invention and the additional active agent need not be prescribed for a patient by the same medical care worker. The additional active agent or agents need not require a prescription. Administration of the compound of the invention or the at least one additional active agent can occur via any appropriate route, for example, oral tablets, oral capsules, oral liquids, inhalation, injection, suppositories or topical contact.

"Treatment," as used herein includes providing a compound of the invention sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibit the disease, i.e. arrest its development; and (c) relieve the disease, i.e., causing regression of the disease.

A "therapeutically effective amount" of a pharmaceutical combination of this invention means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a convention method for determining viral RNA levels such as the Roche TaqMan assay. In certain preferred embodiments treatment reduces HCV RNA levels below the limit of quantitation (30 IU/mL, as measured by the Roche TaqMan® assay) or more preferably below the limit of detection (10 IU/mL, Roche TaqMan).

A significant increase or reduction in the detectable level of virus or viral antibodies is any detectable change that is statistically significant in a standard parametric test of statistical significance such as Student's T-test, where $p<0.05$.

II. Specific Embodiments of the Invention

In addition to compounds of Formula IA and IB, described in the summary of invention section, the invention also includes compounds of Formula IA and IB, in which the variables A, R, and $R_1$ to $R_7$ carry any of the following definitions.

In one embodiment A, Q, $R_3$ to $R_7$, and [U] carry the following definitions and the remaining variables carry the definitions set forth above:

A is a group of the formula:

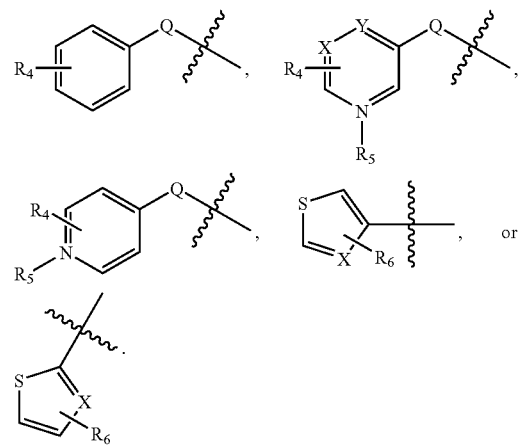

In this definition of A:

Q is absent;

$R_3$ is hydrogen or halogen;

$R_4$ represents 0 or 1 or more substituents independently chosen from (a) and (b) and 0 or 1 substituents chosen from (c): (a) halogen, hydroxyl, cyano, —$CONH_2$, $C_1$-$C_2$haloalkyl, and $C_1$-$C_2$haloalkoxy; (b) $C_1$-$C_4$alkyl and $C_1$-$C_4$alkoxy, each of which is substituted with 0 or 1 substituents independently chosen from hydroxyl, amino, cyano, and mono- and di-$C_1$-$C_2$alkylamino; and (c) mono- and di-$C_1$-$C_4$alkylamino, mono- and di-$C_1$-$C_4$alkylcarboxamide, $C_2$-$C_4$alkanoyl, and (5- or 6-membered heterocycloalkyl)$C_0$-$C_2$alkyl;

Any two $R_4$ groups, covalently bound to adjacent atoms, may be joined to form a 5-membered heterocyclic group containing 1 or 2 additional heteroatoms independently chosen from N, O, and S, wherein the 5-membered heterocyclic group is optionally substituted;

$R_5$ is absent;

$R_6$ is 0 or 1 or more substituents independently chosen from halogen, hydroxyl, cyano, —$CONH_2$, $C_1$-$C_2$haloalkyl, $C_1$-$C_2$haloalkoxy, $C_1$-$C_4$alkyl, $C_1$-$C_4$alkoxy, and mono- and di-$C_1$-$C_4$alkylamino;

$R_7$ is 0 substituents; and

[U] is phenyl, pyridyl, thienyl, $C_3$-$C_7$cycloalkyl, or 5- or 6-membered heterocycloalkyl containing 1 nitrogen atom and 0 or 1 additional heteroatoms chosen from O, S, and N; where each [U] group is substituted with 0 to 2 groups independently chosen from halogen, $C_1$-$C_2$alkyl, and $C_1$-$C_2$alkoxy.

The $R_1$ and $R_2$ Variables $R_1$ and $R_2$ may carry any of the following definitions or meet any of the following conditions.

(1) $R_1$ is in the para position and $R_2$ is absent, or $R_1$ is in the para position and $R_2$ is a single substituent in the meta position.

(2) $R_1$ is in the para position and $R_2$ is a trifluormethyl substituent in the meta position.

(3) $R_1$ is in the para position and is a (5- or 6-membered heteroaryl)$C_0$-$C_4$alkyl or (5- or 6-membered heteroaryl)$C_0$-$C_4$alkoxy, wherein the 5- or 6-membered heteroaryl is thienyl, thiazolyl, imidazolyl, oxazolyl, or pyridyl.

(4) $R_1$ is $C_4$-$C_{10}$alkoxy, $C_4$-$C_{10}$alkyl, $C_4$-$C_{10}$alkylamino, or di-($C_1$-$C_6$)($C_4$-$C_{10}$)alkylamino, or ($C_3$-$C_7$cycloalkyl)$C_0$-$C_4$alkyl, and $R_2$ is 0 or 1 substituent chosen from halogen, hydroxyl, amino, cyano, $C_1$-$C_2$alkyl, $C_1$-$C_2$alkoxy, $C_1$-$C_2$haloalkyl, and $C_1$-$C_2$haloalkoxy. Or, $R_1$ is $C_6$-$C_{10}$alkyl or $C_6$-$C_{10}$alkoxy; $C_6$-$C_{10}$alkylamino, or di-($C_1$-$C_6$)($C_4$-$C_{10}$)alkylamino, or ($C_3$-$C_7$cycloalkyl)$C_0$-$C_4$alkyl, and $R_2$ is 0 or 1 substituent chosen from halogen, hydroxyl, amino, cyano, $C_1$-$C_2$alkyl, $C_1$-$C_2$alkoxy, $C_1$-$C_2$haloalkyl, and $C_1$-$C_2$haloalkoxy.

(5) $R_1$ is $C_4$-$C_{10}$alkoxy, $C_4$-$C_{10}$alkyl, $C_4$-$C_{10}$alkylamino, or di-($C_1$-$C_6$)($C_4$-$C_{10}$)alkylamino, or ($C_3$-$C_7$cycloalkyl)$C_0$-$C_4$alkyl, and $R_2$ is 0 or 1 substituent chosen from halogen, hydroxyl, amino, cyano, $C_1$-$C_2$alkyl, $C_1$-$C_2$alkoxy, $C_1$-$C_2$haloalkyl, and $C_1$-$C_2$haloalkoxy; wherein $R_1$ is in the para position and $R_2$ is in the meta position. Or, $R_1$ is $C_6$-$C_{10}$alkoxy, $C_6$-$C_{10}$alkyl, $C_6$-$C_{10}$alkylamino, or di-($C_1$-$C_6$)($C_4$-$C_{10}$)alkylamino, or ($C_3$-$C_7$cycloalkyl)$C_0$-$C_4$alkyl, and $R_2$ is 0 or 1 substituent chosen from halogen, hydroxyl, amino, cyano, $C_1$-$C_2$alkyl, $C_1$-$C_2$alkoxy, $C_1$-$C_2$haloalkyl, and $C_1$-$C_2$haloalkoxy; wherein $R_1$ is in the para position and $R_2$ is in the meta position.

(6) $R_1$ is $C_6$-$C_{10}$alkyl or $C_6$-$C_{10}$alkoxy and $R_2$ is 0 or 1 substituent chosen from fluoro, trifluoromethyl, and trifluoromethoxy; wherein $R_1$ is in the para position and $R_2$ is in the meta position.

The A Variable

"A" may carry any of the following definitions.

(1) A is a group of the formula:

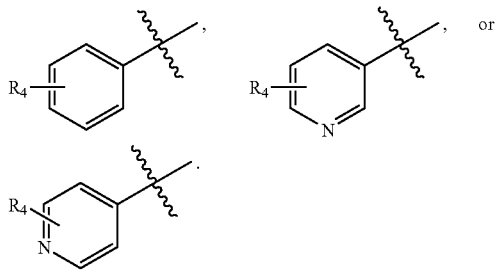

(2) A is a group of the formula

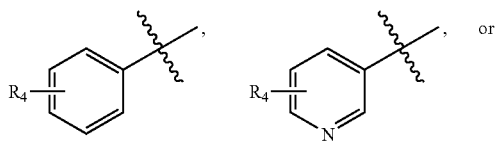

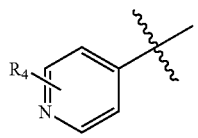
wherein $R_4$ is 0, 1, or 2 substituents independently chosen from (a) and (b) and 0 or 1 substituents chosen from (c):

(a) halogen, hydroxyl, cyano, and —$CONH_2$;

(b) $C_1$-$C_4$alkyl and $C_1$-$C_4$alkoxy, each of which is substituted with 0 or 1 substituents independently chosen from hydroxyl, amino, cyano, and mono- and di-$C_1$-$C_2$alkylamino; or (c) mono- and di-$C_1$-$C_2$alkylamino, mono- and di-$C_1$-$C_2$alkylcarboxamide, and (5- or 6-membered heterocycloalkyl)$C_0$-$C_2$alkyl.

(3) A is a group of the formula:

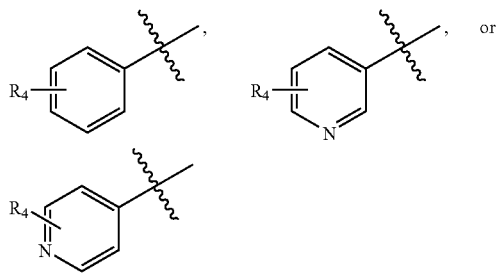

and $R_4$ is 0, 1, or 2 substituents independently chosen from hydroxyl, halogen, cyano, —$CONH_2$, $C_1$-$C_2$alkyl, and $C_1$-$C_2$alkoxy.

(4) A is a group of the formula:

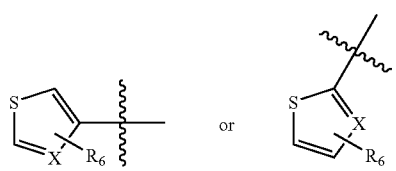

where $R_6$ is 0, 1, or 2 substituents independently chosen from halogen, hydroxyl, $C_1$-$C_2$alkyl, and $C_1$-$C_2$alkoxy.

The R Variable

The variable R may carry any of the following definitions.

(1) R is a group of the formula

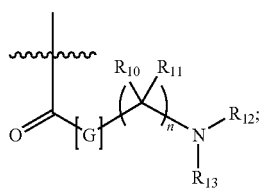

[G] is O or absent; n is 1, 2, or 3; $R_{10}$ is H or $C_1$-$C_4$alkyl; $R_{11}$ is H; and $R_{12}$ and $R_{13}$ are hydrogen, methyl, or ethyl.

(2) R is a group of the formula

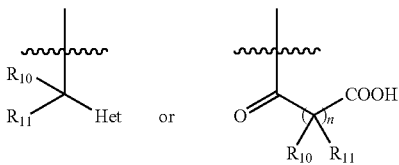

where
$R_{10}$ is hydrogen or $C_1$-$C_4$alkyl;
$R_{11}$ is hydrogen or methyl; or
n is an integer from 1 to 3, independently chosen at each occurrence;
Het is a pyridyl, imidazolyl, dioxolyl, oxazolyl, pyrrolyl, furanyl, or thienyl group each of which Het substituted with 0 to 3 substituents independently chosen from halogen, hydroxyl, amino, cyano, oxo, $C_1$-$C_2$alkyl, $C_1$-$C_2$alkoxy, and mono- and di-$C_1$-$C_2$alkylamino.

(3) R is a group of the formula

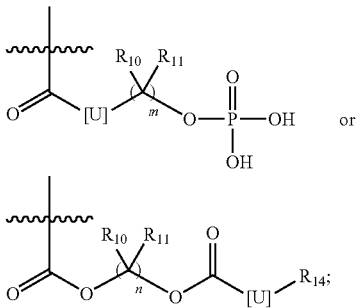

$R_{10}$ is hydrogen or $C_1$-$C_4$alkyl; $R_{11}$ is hydrogen or methyl; m is an integer from 1 to 3; n is an integer from 1 to 3; [U] is phenyl or pyridyl; each of which is substituted with 0 to 2 groups independently chosen from halogen, hydroxyl, amino, cyano, $C_1$-$C_2$alkyl, and $C_1$-$C_2$alkoxy.

(4) R is a group of the formula

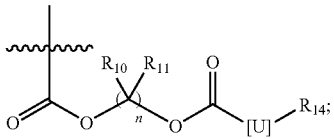

where n is 1, 2, or 3; $R_{10}$ is independently chosen on each occasion from hydrogen, amino, and $C_1$-$C_4$alkyl; where not more than one $R_{10}$ is amino; $R_{11}$ is hydrogen or methyl; [U] is absent; $R_{14}$ is hydrogen or is $R_{14}$ is $C_1$-$C_4$alkyl substituted 0 or 1 substituents chosen from —COOH, —OPO(OH)$_2$, amino, hydroxyl, mono- and di-$C_1$-$C_2$alkylcarboxamide, and mono- and di-$C_1$-$C_4$alkylamino.

(5) R is a group of the formula

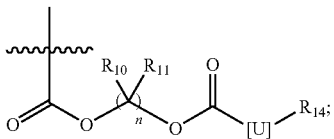

where n is 1, 2, or 3; $R_{10}$ is independently hydrogen or amino and only one $R_{10}$ is amino; $R_{11}$ is hydrogen; and $R_{14}$ is hydrogen or $R_{14}$ is $C_1$-$C_4$alkyl substituted with one amino or $C_1$-$C_4$alkyl substituted with —NH(C=O)CH$_3$ or —NH(C=O)CH$_2$CH$_3$.

(6) R is a group of the formula

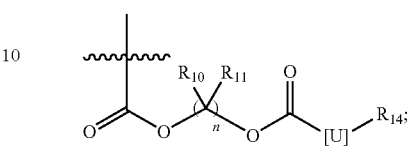

where n is 1, 2, or 3; $R_{10}$ is independently chosen on each occasion from hydrogen and amino, and not more than one $R_{10}$ is amino; $R_{11}$ is hydrogen or methyl; [U] is phenyl or pyridyl; $R_{14}$ is hydrogen or is $R_{14}$ is $C_1$-$C_4$alkyl substituted 0 or 1 substituents chosen from amino, mono- and di-$C_1$-$C_4$alkylamino, and —OPO(OH)$_2$.

(7) R is a group of the formula

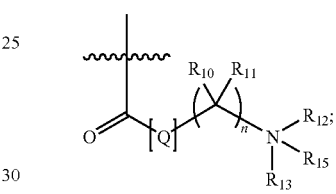

Q is O or absent; n is 1, 2, or 3; $R_{10}$ is H or $C_1$-$C_4$alkyl; $R_{11}$ is H; $R_{12}$ and $R_{13}$ are hydrogen, methyl, or ethyl; and $R_{15}$ is absent or methyl.

(8) R is a group of the formula

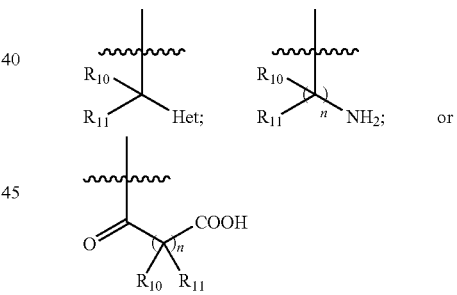

where $R_{10}$ is hydrogen or $C_1$-$C_4$alkyl; $R_{11}$ is hydrogen or methyl; or n is an integer from 1 to 3, independently chosen at each occurrence; and Het is a pyridyl, imidazolyl, dioxolyl, oxazolyl, pyrrolyl, furanyl, or thienyl group each of which Het substituted with 0 to 3 substituents independently chosen from halogen, hydroxyl, amino, cyano, oxo or $C_1$-$C_2$alkyl, $C_1$-$C_2$alkoxy, $C_1$-$C_2$mono- and di-alkylamino.

(9) R is

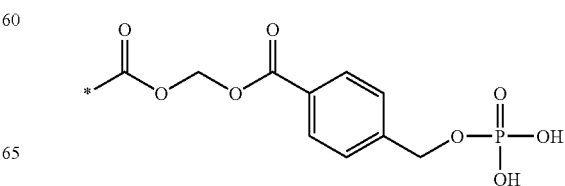

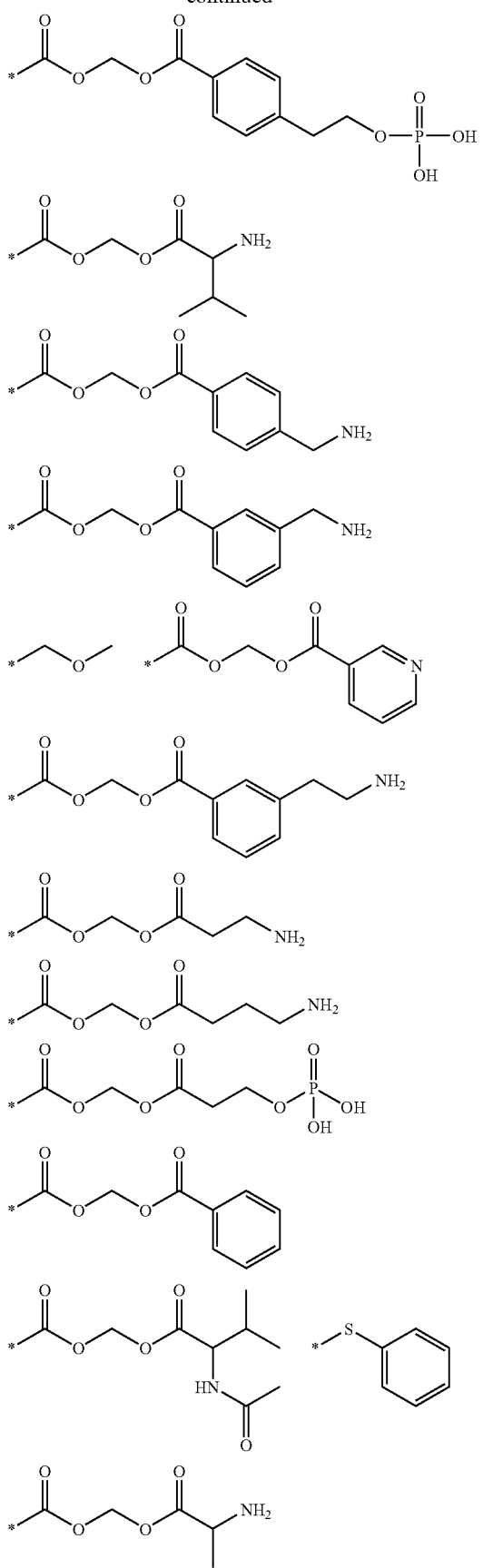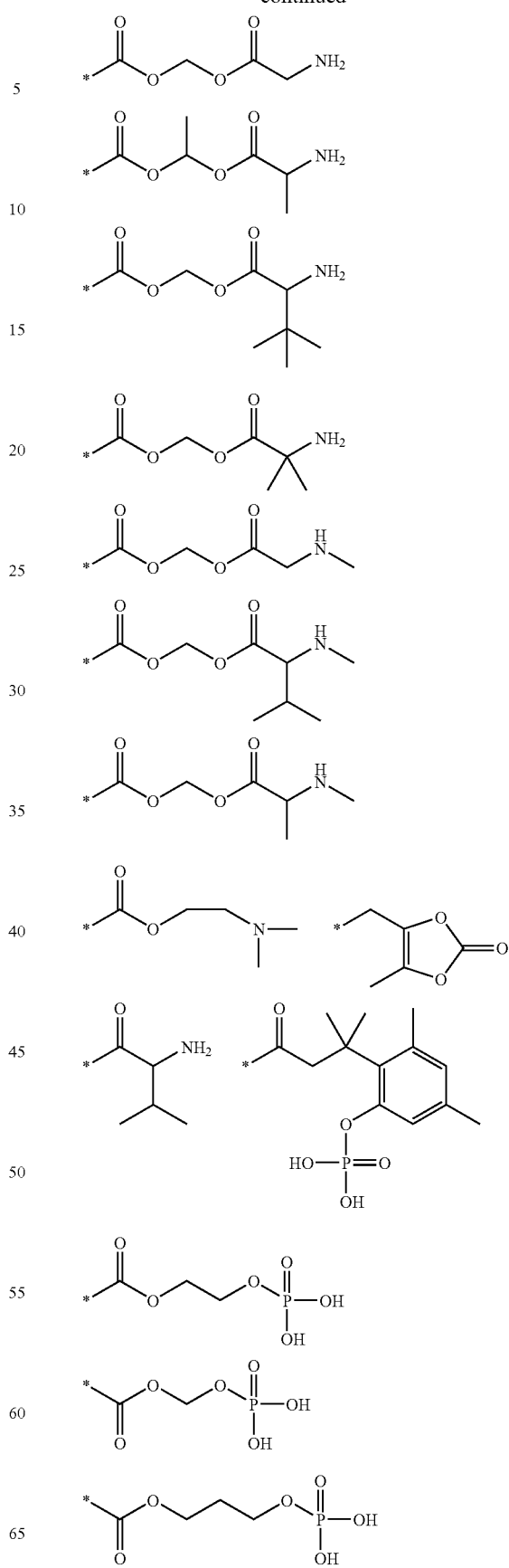

-continued

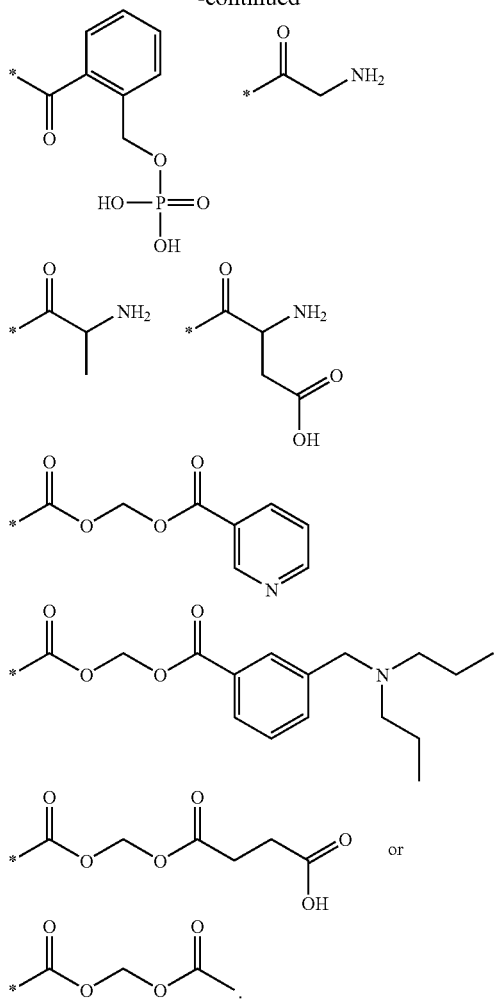

The invention includes compounds of Formula IA and IB in which the variables e.g. A, R, $R_1$, $R_2$, and $R_3$, carry any combination of the definitions set forth above for these variables which The invention includes compounds of the formula:

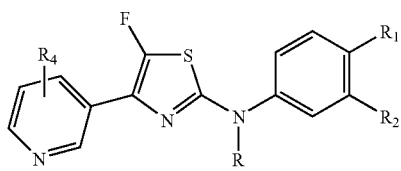

wherein $R_1$ is $C_6$-$C_{10}$alkoxy or $C_6$-$C_{10}$alkyl; $R_2$ is fluoro, trifluoromethyl, or trifluoromethoxy; $R_4$ is 0, 1, or 2 substituents independently chosen from hydroxyl, halogen, cyano, —$CONH_2$, $C_1$-$C_2$alkyl, and $C_1$-$C_2$alkoxy; and R may carry any of the definitions set forth above for this variable.

Other preferred compounds include compounds of Formula I and Formula II in which A is unsubstituted 3-pyridyl, $R_1$ is a n-octyl at the para position, $R_2$ is a meta position trifluoromethyl group, $R_3$ is fluoro, and R carries any of the definitions set forth herein for that variable.

The above compounds are listed only to provide examples that may be used in the methods of the invention. Based upon the instant disclosure, the skilled artisan would recognize other compounds intended to be included within the scope of the presently claimed invention that would be useful in the methods recited herein.

Methods of HCV Inhibition

Another aspect of the invention relates to methods of inhibiting the activity of HCV, comprising the step of treating (e.g., contacting, administering, etc.) a sample suspected of containing HCV with at least one compound of the invention. Compounds of the invention may act as inhibitors of HCV, as intermediates for such inhibitors, or have other utilities as described herein.

Many organisms contain HCV. The compounds of this invention are useful in the treatment or prophylaxis of conditions associated with HCV infection in animals or in man. Thus, in certain aspects, methods for treating or preventing HCV infection are provided, comprising administering a therapeutic or prophylactic amount of at least one compound of the invention to a subject in need thereof.

In certain aspects, the inhibitors may generally bind to locations on the surface or in a cavity of the liver where HCV is present. Compositions binding in the liver may bind with varying degrees of reversibility. Those compounds binding substantially irreversibly are ideal candidates for use in this method of the invention. Once labeled, the substantially irreversibly binding compositions are useful as probes for the detection of HCV. Accordingly, the invention relates to methods of detecting HCV in a sample suspected of containing HCV comprising the steps of: treating a sample suspected of containing HCV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures. In certain embodiments, samples include cell and tissue samples, and subjects, including humans.

The treating step of the invention may comprises adding at least one compound of the invention to the sample, or it may comprises adding a precursor of the at least one compound to the sample. The addition step comprises any method of administration as described herein.

If desired, the activity of HCV after application of the compound(s) can be observed by any method, including direct and indirect methods of detecting HCV activity. Quantitative, qualitative, and semiquantitative methods of determining HCV activity are all contemplated. Typically one of the screening methods described herein may be applied, however, any other method such as observation of the physiological properties of a living organism may also be applicable.

However, in screening compounds capable of inhibiting HCV it should be kept in mind that the results of enzyme assays may not correlate with cell culture assays. Thus, in certain aspects, a cell-based assay may preferably be the primary screening tool.

More particularly, as described herein, certain compounds of the invention are potent inhibitors of HCV replication and/or proliferation. The activity of compounds of the invention can be confirmed in in vitro assays suitable for measuring inhibition of viral or retroviral replication and/or proliferation. The assays may investigate any parameter that is directly or indirectly under the influence of HCV, including, but not limited to, protein-RNA binding, translation, transcription, genome replication, protein processing, viral particle formation, infectivity, viral transduction, etc. Such assays are well known in the art. Regardless of the parameter being investigated, in one embodiment, to examine the extent of inhibition, samples, cells, tissues, etc. comprising an HCV replicon or HCV RNA are treated with a potential inhibitory compound (test compound) and the value for the parameter compared to control cells (untreated or treated with a vehicle or other placebo). Control samples are assigned a relative activity value of 100%. Inhibition may be achieved when the activity value of the test compound relative to the control is about 90%, preferably 50%, and more preferably 25-0%.

Alternatively, the extent of inhibition may be determined based upon the $IC_{50}$ of the compound in the particular assay, as will be described in more detail herein.

In one embodiment, the inhibitory activity of the compounds may be confirmed in a replicon assay that assesses the ability of a test compound to block or inhibit HCV replication in replicon cells. One example of a suitable replicon assay is the liver cell-line Huh 7-based replicon assay described in Lohmann et al., 1999, Science 285:110-113. A specific example of this replicon assay utilizes luciferase translation. In one embodiment of this assay, the amount of test compound that yields a 50% reduction in translation as compared to a control cell (IC50, EC50, and/or CC50) may be determined. An replicon assay is provided in Example 7 below.

Alternatively, the inhibitory activity of the compounds may be confirmed using a quantitative Western immunoblot assay utilizing antibodies specific for HCV non-structural proteins, such as NS3, NS4A NS5A and NS5B. In one embodiment of this assay, replicon cells are treated with varying concentrations of test compound to determine the concentration of test compound that yields a 50% reduction in the amount of a non-structural protein produced as compared to a control sample (IC50, EC50, and/or CC50). A single non-structural protein may be quantified or multiple non-structural proteins may be quantified. Antibodies suitable for carrying out such immunoblot assays are available commercially (e.g., from BIODESIGN International, Saco, Me.).

Alternatively, the inhibitory activity of the compounds may be confirmed in an HCV infection assay, such as the HCV infection assay described in Fournier et al., 1998, J. Gen. Virol. 79(10):2367:2374, the disclosure of which is incorporated herein by reference. In one embodiment of this assay, the amount of test compound that yields a 50% reduction in HCV replication or proliferation as compared to a control cell (IC50, EC50, and/or CC50) may be determined. The extent of HCV replication may be determined by quantifying the amount of HCV RNA present in HCV infected cells. An exemplary replicon assay is provided in Example 7 of this application. Compounds active against HCV typically exhibit an EC50 of 5 micromolar or less in this assay.

As yet another example, the inhibitory activity of the compounds may be confirmed using an assay that quantifies the amount of HCV RNA transcribed in treated replicon cells using, for example, a Taqman assay (Roche Molecular, Alameda, Calif.). In one embodiment of this assay, the amount of test compound that yields a 50% reduction in transcription of one or more HCV RNAs as compared to a control sample (IC50, EC50, and/or CC50) may be determined.

Regardless of the assay used, active compounds are generally those which exhibit an IC50, EC50, and/or CC50 in at least one assay in the range of about less than 25 µM, preferably less than about 15 µM, about 10 µM, about 5 µM, or about 1 µM. Compounds which exhibit an IC50, EC50, and/or CC50, for example, in the range of less than about 10 µM, 5 µM, 1 µM, 0.10 µM, 0.50 µM, or even lower, are particularly useful for as therapeutics or prophylactics to treat or prevent HCV infections.

As discussed herein, due to their ability to inhibit HCV replication, the compounds of the invention and/or compositions thereof can be used in a variety of contexts. For example, the compounds of the invention can be used as controls in in vitro assays to identify additional more or less potent anti-HCV compounds. As another example, the compounds of the invention and/or compositions thereof can be used as preservatives or disinfectants in clinical settings to prevent medical instruments and supplies from becoming infected with HCV virus. When used in this context, the compound of the invention and/or composition thereof may be applied to the instrument to be disinfected at a concentration that is a multiple of the measured IC50 for the compound.

In a specific embodiment, the compounds and/or compositions may also be used to "disinfect" organs for transplantation. For example, a liver or portion thereof being prepared for transplantation can be perfused with a solution comprising an inhibitory compound of the invention prior to implanting the organ into the recipient. This method has proven successful with lamuvidine (3TC, Epivir™, Epivir-HB™) for reducing the incidence of hepatitis B virus (HBV) infection following liver transplant surgery/therapy. Quite interestingly, it has been found that such perfusion therapy not only protects a liver recipient free of HBV infection (HBV−) from contracting HBV from a liver received from an HBV+ donor, but it also protects a liver from an HBV− donor transplanted into an HBV+ recipient from attack by HBV. The compounds of the invention may be used in a similar manner prior to organ or liver transplantation.

Certain compounds disclosed herein, including the compounds of Formula II-A and II-B are prodrugs. The compounds typically do not exhibit anti-HCV activity in in vitro assays of HCV activity such as replicon replication assays. However prodrug compounds are modified in vivo to produce a parent compound having known anti-HCV activity. Often prodrug compounds are have advantages over their parent drug compounds. Anti-HCV activity of prodrug compounds is established by quantitating the blood or plasma levels of parent compound after prodrug administration. In vivo blood or plasma levels are reported as $C_{max}$ (maximum blood or plasma concentration) and AUC (Area Under Curve from zero to infinity, a measure of total drug exposure). Methods of measuring $C_{max}$, AUC, and other pharmacokinetic parameters in dogs and rats are provided in Example 7.

For example prodrug compounds are often better absorbed in vivo leading to higher overall blood or plasma levels of parent drug compound.

III. Pharmaceutical Preparations

Compounds of the invention can be administered as the neat chemical, but are preferably administered as a pharmaceutical composition. Accordingly, the invention provides pharmaceutical formulations comprising a compound or pharmaceutically acceptable salt of the invention, together with at least one pharmaceutically acceptable carrier.

Compounds of the invention may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorings, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Binders are substances that bind or "glue" powders together and make them cohesive by forming granules, thus serving as the "adhesive" in the formulation. Binders add cohesive strength to that already available in the diluent or bulking agent. Examples of binders include starch, gelatin, natural sugars, corn sweeteners, natural and synthetic gums such as acacia, sodium alginate, carboxymethylcellulose, polyethylene glycol and waxes. The amount of binder in the composition can range, for example, from about 2 to about 20% by weight of the composition, or from about 3 to about 10% by weight, even more preferably from about 3 to about 6% by weight.

Diluents include sugars such as lactose, sucrose, mannitol and sorbitol; starches derived from wheat, corn, rice and potato; and celluloses such as microcrystalline cellulose. The amount of diluent in the composition may be, for example, about 10 to about 90% by weight of the total composition, about 25 to about 75%, about 30 to about 60% by weight, or about 12 to about 60%.

Disintegrants are materials added to a pharmaceutical composition to help it break apart (disintegrate) and release the active agent. Suitable disintegrants include starches; including "cold water soluble" modified starches such as sodium carboxymethyl starch; natural and synthetic gums such as locust bean, karaya, guar, and tragacanth gum and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range, for example, from about 2 to about 15% by weight of the composition or from about 4 to about 10% by weight.

Lubricants are substances added to a pharmaceutical formulation to enable the tablet, granules, etc. after it has been compressed, to release from the; mold or die by reducing friction or wear. Examples of lubricants useful in pharmaceutical dosage forms include boric acid, sodium benzoate, sodium acetate, sodium chloride, and the like. Lubricants are usually added at the very last step before tablet compression, since they must be present on the surfaces of the granules and in between them and the parts of the tablet press. The amount of lubricant in the composition can range, for example, from about 0.1 to about 5% by weight of the composition, from about 0.5 to about 2%, or from about 0.3 to about 1.5% by weight. The amount of compound or salt of the invention in a unit dose may be generally varied or adjusted from about 1.0 milligram to about 1,000 milligrams, from about 1.0 to about 900 milligrams, from about 1.0 to about 500 milligrams, or from about 1 to about 250 milligrams, according to the particular application and the potency of the compound. The actual dosage employed may be varied depending upon the patient's age, sex, weight and severity of the condition being treated.

Pharmaceutical compositions formulated for oral administration are often preferred. These compositions contain between 0.1 and 99% of a compound of the invention and usually at least about 5% (weight %) of a compound of the invention. Some embodiments contain from about 25% to about 50% or from 5% to 75% of a compound of invention.

Liquids Formulations

Compounds of the invention can be incorporated into oral liquid preparations such as aqueous or oily suspensions, solutions, emulsions, syrups, tinctures, syrups, or elixirs, for example. Moreover, formulations containing these compounds can be presented as a dry product, e.g. as granules or powders, for constitution with water or other suitable vehicle before use. Typical components of carriers for syrups, elixirs, emulsions and suspensions include ethanol, glycerol, propylene glycol, polyethylene glycol, liquid sucrose, sorbitol and water. Liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid). Oral formulations may contain demulcent, flavoring agents, sweetening agents, such as sucrose or saccharin, taste-masking agents, and coloring agents.

Suspensions

Aqueous suspensions contain the active material(s) in admixture with excipients suitable for the manufacture of aqueous suspensions. Such excipients are suspending agents, for example AVICEL RC-591, sodium carboxymethylcellulose, methylcellulose, hydropropylmethylcellulose, sodium alginate, polyvinylpyrrolidone, gum tragacanth and gum acacia; dispersing or wetting agents, for example lecithin and polysorbate 80. The aqueous suspensions may also contain one or more preservatives, for example ethyl, n-propyl p-hydroxybenzoate, methyl parabens, propyl parabens, and sodium benzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard or soft shell capsules. A capsule is a dosage form administered in a special container or enclosure containing an active agent. The active agent may be present in solid, liquid, gel, or powder form, or any other pharmaceutically acceptable form. A capsule shell may be made of methyl cellulose, polyvinyl alcohols, or denatured gelatins or starch or other material. Hard shell capsules are typically made of blends of relatively high gel strength bone and pork skin gelatins. Soft shell capsule shells are often made of animal or plant gelatins. The capsule itself may contain small amounts of dyes, opaquing agents, plasticizers and preservatives.

The active agent in a capsule may be mixed with an inert solid diluent, for example, calcium carbonate, calcium phosphate or kaolin, or in the case of soft gelatin capsules the active ingredient may be mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of the invention may be administered parenterally in a sterile medium. Parenteral administration includes subcutaneous injections, intravenous, intramuscular, intrathecal injection or infusion techniques. The drug, depending on the vehicle and concentration used, can either be suspended or dissolved in the vehicle. Advantageously, adjuvants such as local anesthetics, preservatives and buffering agents can be dissolved in the vehicle. In compositions for parenteral administration the carrier typically comprises least about 90% by weight of the total composition.

IV. Methods of Treatment

The invention includes methods of preventing and treating hepatitis C infections, by providing an effective amount of a compound of the invention to patient at risk for hepatitis C infection or infected with a hepatitis C virus.

The pharmaceutical combinations disclosed herein are useful for preventing and treating hepatitis C infections in patients. An effective amount of a pharmaceutical combination of the invention may be an amount sufficient to (a) prevent hepatitis C or a symptom of a hepatitis C from occurring in a patient who may be predisposed to hepatitis C but has not yet been diagnosed as having it or prevent diseases that may be associated with or caused by a primary hepatitis C infection (such as liver fibrosis that can result in the context of chronic HCV infection); (b) inhibit the progression of hepatitis C; and (c) cause a regression of the hepatitis C infection. An amount of a pharmaceutical composition effect to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

Symptoms of hepatitis C that may be affected by an effective amount of a pharmaceutical combination of the invention include decreased liver function, fatigue, flu-like symptoms: fever, chills, muscle aches, joint pain, and headaches, nausea, aversion to certain foods, unexplained weight loss, psychological disorders including depression, tenderness in the abdomen, and jaundice.

"Liver function" refers to a normal function of the liver, including, but not limited to, a synthetic function including synthesis of proteins such as serum proteins (e.g., albumin, clotting factors, alkaline phosphatase, aminotransferases (e.g., alanine transaminase, aspartate transaminase), 5'-nucleosidase, y glutaminyltranspeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

An effective amount of a combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

The invention also includes using pharmaceutical combinations comprising a compound of the invention and at least one additional active agent in prophylactic therapies. In the context of prophylactic or preventative treatment an effective amount of a compound of the invention is an amount sufficient to significantly decrease the patient's risk of contracting a hepatitis C infection.

Methods of treatment include providing certain dosage amounts of a compound of the invention and the at least one additional active agent to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the patient treated and the particular mode of administration. Dosage unit forms will generally contain between from about 1 mg to about 500 mg of each active agent. In certain embodiments 25 mg to 500 mg, or 25 mg to 200 mg of a compound of the invention are provided daily to a patient. When the additional active agent is NM 283 (valopicitabine), 100 mg to 1000 mg/day, or 200 mg to 800 mg/day, or 200 to 400 mg/day of either of those agents are typically provided to the patient. When the additional active agent is VX-950, 1000 mg to 3750 mg/day, or 1200 mg to 1800 mg/day are administered to the patient. Treatment regiments in which VX-950 is an additional active agent and about 350 to about 450 mg or about 700 to about 800 mg of VX-950 are administered to a patient three times per day or about 350 to about 450 mg or about 700 to about 800 mg is administered every 12 hours are particularly included in the invention.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

V. Combination Methods

Compounds of the invention may also be used in combination with other active ingredients useful in the inhibition of HCV or other co-morbid indications, as recognized by those skilled in the art. Such combinations are selected based on the condition to be treated, cross-reactivities of ingredients and pharmaco-properties of the combination.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

The invention includes methods of treatment in which a compound or salt of the invention is provided together with one or more additional active agents. In certain embodiments the active agent (or agents) is an HCV protease inhibitor or HCV polymerase inhibitor. For example the protease inhibitor may be telaprevir (VX-950) and the polymerase inhibitor may be valopicitabine, or NM 107, the active agent which valopicitabine is converted into in vivo.

According to the methods of the invention, the compound of the invention and an additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the compound of The invention and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In certain embodiments method of treatment includes providing a patient with a compound of Formula I and an interferon such as a pegylated interferon or interferon gamma. The interferon may be the only compound provided with the compound of the invention or may be provided with an additional active agent that is not an interferon.

The invention methods of treatment and pharmaceutical combinations including compounds of the invention any one or combination of the following compounds and substances as an additional active agent:

Caspase inhibitors: IDN 6556 (Idun Pharmaceuticals)
Cyclophilin Inhibitors: NIM811 (Novartis) and DEBIO-025 (Debiopharm) Cytochrome P450 monooxygenase inhibitors: ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole Glucocorticoids: hydrocortisone, cortisone, prednisone, prednisolone, methylprednisolone, triamcinolone, paramethasone, betamethasone, and dexamethasone Hematopoietins: hematopoietin-1 and hematopoietin-2. Other members of the hematopoietin superfamily such as the various colony stimulating factors (e.g. (e.g. G-CSF, GM-CSF, M-CSF), Epo, and SCF (stem cell factor)

Homeopathic Therapies: Milk Thistle, silymarin, ginseng, glycyrrhizin, licorice root, schisandra, vitamin C, vitamin E, beta carotene, and selenium Immunomodulatory compounds: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha nl from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEGINTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), un-pegylated interferon alpha, alpha interferon, and its analogs, and synthetic thymosin alpha 1 (ZADAXIN, SciClone Pharmaceuticals Inc.)

Immunosupressants: sirolimus (RAPAMUNE, Wyeth)

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (XTL), HuMax-HepC (Genmab), Hepatitis C Immune Globin (human) (CIVACIR, Nabi Biopharmceuticals)

Nucleoside analogues: Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), and viramidine (Valeant Pharmaceuticals), an amidine prodrug of ribavirin. Combinations of nucleoside analogues may also be employed.

Non-nucleoside inhibitors: PSI-6130 (Roche/Pharmasset), delaviridine (RESCRIPTOR, Pfizer), and HCV-796 (Viropharm)

P7 protein inhibitor: amantadine (SYMMETREL, Endo Pharmaceuticals, Inc.)

Polymerase inhibitors: NM283 (valopicitabine) (Idenix) and NM 107 (Idenix).

Protease inhibitors: BILN-2061 (Boehringer Ingelheim), GW-433908 (prodrug of Amprenavir, Glaxo/Vertex), indinavir (CRIXIVAN, Merck), ITMN-191 (Intermune/Array Biopharma), VX950 (Vertex) and combinations comprising one or more of the foregoing protease inhibitors RNA interference: SIRNA-034 RNAi (Sirna Therapeutics)

Therapeutic Vaccines: IC41 (Intercell), IMN-0101 (Imnogenetics), GI 5005 (Globeimmune), Chronvac-C (Tripep/Inovio), ED-002 (Imnogenetics), Hepavaxx C (ViRex Medical)

TNF agonists: adalimumab (HUMIRA, Abbott), entanercept (ENBREL, Amgen and Wyeth), infliximab (REMICADE, Centocor, Inc.)

Tubulin inhibitors: Colchicine

Sphingosine-1-phosphate receptor modulators: FTY720 (Novartis)

TLR agonists: ANA-975 (Anadys Pharmaceuticals), TLR7 agonist (Anadys Pharmaceuticals), CPG10101 (Coley), and TLR9 agonists including CPG 7909 (Coley)

Cyclophilin Inhibitors: NIM811 (Novartis) and DEBIO-025 (Debiopharm)

Patients receiving hepatitis C medications are typically given interferon together with another active agent. Thus methods of treatment and pharmaceutical combinations in which a compound of The invention is provided together with an interferon, such as pegylated interferon alfa 2a, as the additional active agents are included as embodiments. Similarly methods and pharmaceutical combinations in which ribavirin is an additional active agent are provided herein.

VI. Metabolites of Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabeled (e.g., C14 or H3) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HIV-inhibitory activity of their own.

Methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo.

VII. Exemplary Methods of Making the Compounds of the Invention

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

VIII. Synthetic Schemes

General aspects of these exemplary methods are described below and in the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

NMR spectra are recorded at ambient temperature using a Bruker Avance 300 spectrometer ($^1$H at 300.1 MHz and $^{13}$C at 75.5 MHz). The chemical shifts for $^1$H and $^{13}$C are reported in parts per million (δ) relative to external tetramethylsilane and are referenced to signals of residual protons in the deuterated solvent. Analytical HPLC is performed using a Waters X-bridge C 18 150×4.6 mm 3.5 μm column with a 20-min linear gradient elution of increasing concentrations of acetonitrile in water (5 to 95%) containing 0.1% trifluoroacetic acid with a flow rate of 1.0 mL/min and UV detection at 254 nm. Low-resolution mass spectra are recorded on a Thermo Finnigan Surveyor MSQ instrument (operating in APCI mode) equipped with a Gilson liquid chromatograph. Unless noted otherwise, the quasi-molecular ions, [M+H]$^+$, observed in the low-resolution mass spectra are the base peaks.

As shown in the following reaction schemes, the aminothiazoles may be prepared by the reaction between an alpha-haloketone and thiourea. There are several methods known in literature for the synthesis of alpha-haloketone, and a few have been illustrated in scheme 1. However, the invention is not so limited. The thioureas may be prepared from the corresponding amines or anilines by reacting them with thiocarbonyldiimidazole followed by ammonia. Other methods known in literature may also be used to prepare thioureas. The aminothiazoles may then be converted to their corresponding, i) amides, by reacting it with activated carboxylic acids, ii) carbamates, by reacting it with alkoxy/aryloxy carbonylchlorides, iii) ureas, by reacting it with isocyanates and iv) formyl, by reacting it with Formaic acid/Acetic anhydride as shown in scheme 2.

Modifications of each of the exemplary schemes, which will be readily understood by those of skill in the art, may be needed to produce particular compounds of the invention. The above-cited citations describing suitable methods of organic synthesis are applicable to such modifications. This invention is further illustrated by examples, which appear in the following section, and should not be construed as limiting.

Scheme 1
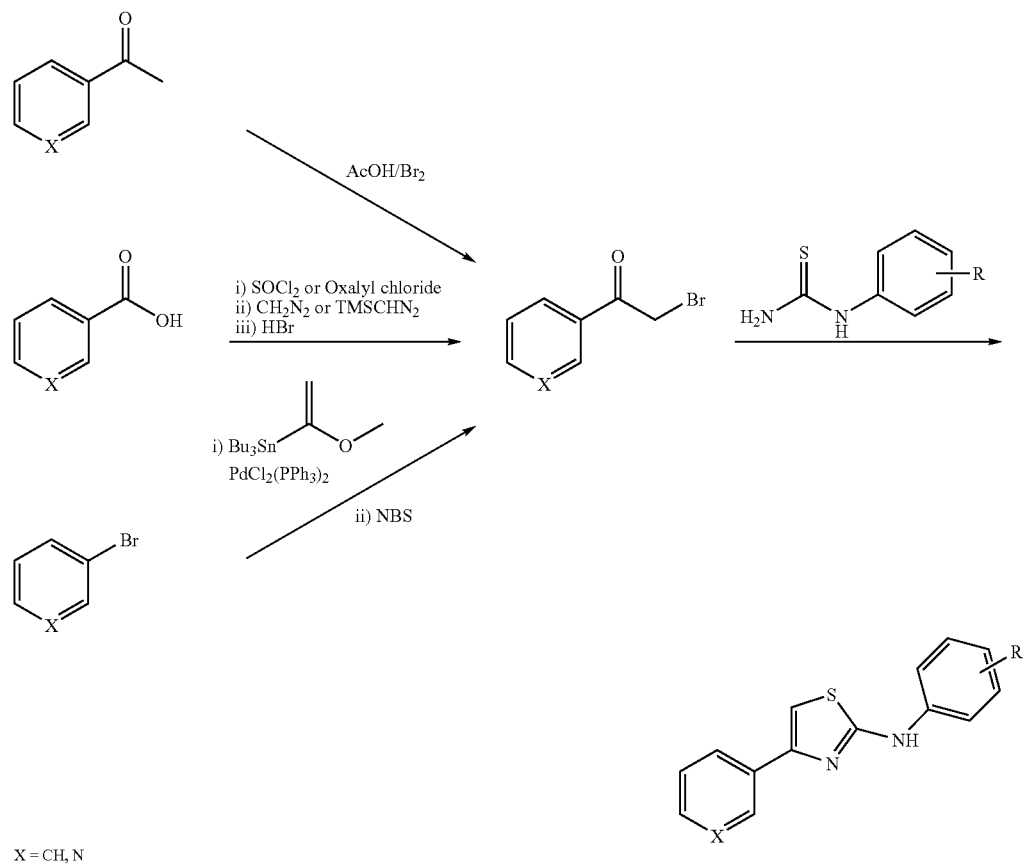
X = CH, N
Scheme 2
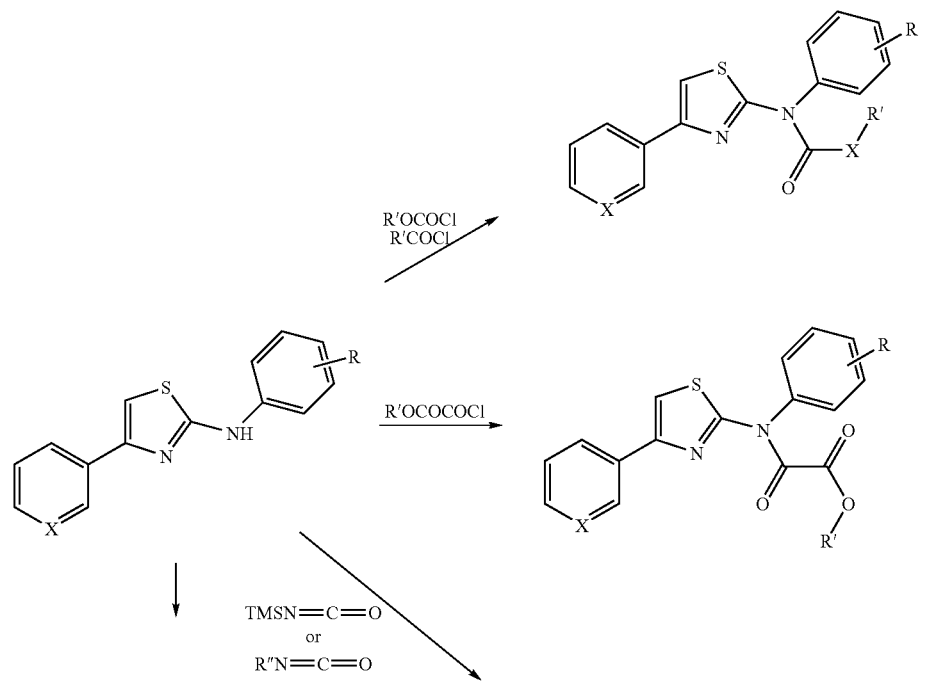

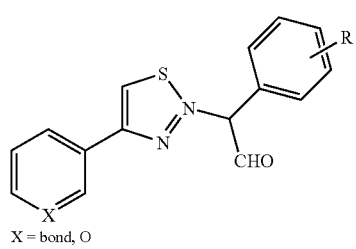
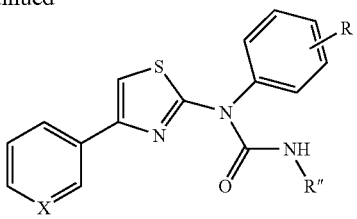

X = bond, O

Schemes 3 and 4 then describe the synthesis of carboxylic acid substituted thiazoles and aminomethylene substituted thiazoles.

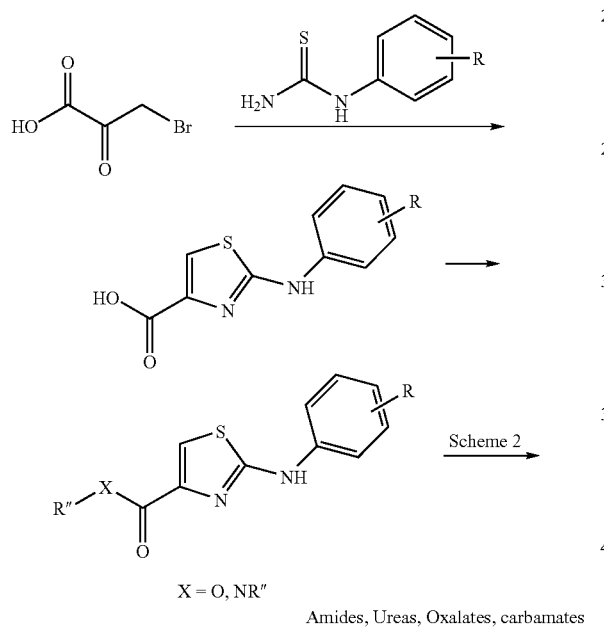

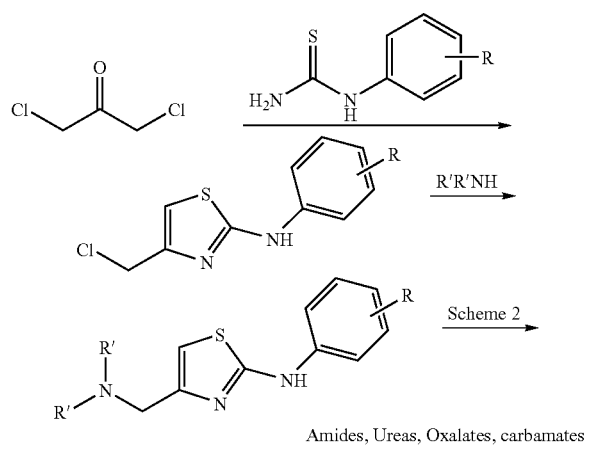

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

EXAMPLES

Abbreviations

The following chemical abbreviations are used in Examples 1 to 4. Additional abbreviations used in these examples will be familiar to those of skill in the art of organic chemical synthesis.

ACN Acetonitrile
AcOH Acetyl Alcohol
DCM Dichloromethane
DMF Dimethyl formamide
$Et_3N$ Triethylamine
EtOAc Ethyl Acetate
EtOH Ethanol
MeOH Methanol
$Pd(PPh_3)_2Cl_2$ Dichlorobis(triphenylphosphine)palladium (II)
SM Starting Material
TCDI Thiocarbonyl Diimidazole
TEA Triethylamine
TFA Trifluoroacetic acid Example 1

Synthesis of Exemplary Compounds

General procedures for the synthesis of the compounds below is shown in Scheme 5. Additional compounds were synthesized according to similar procedures, as shown in TABLE A.

Scheme 5

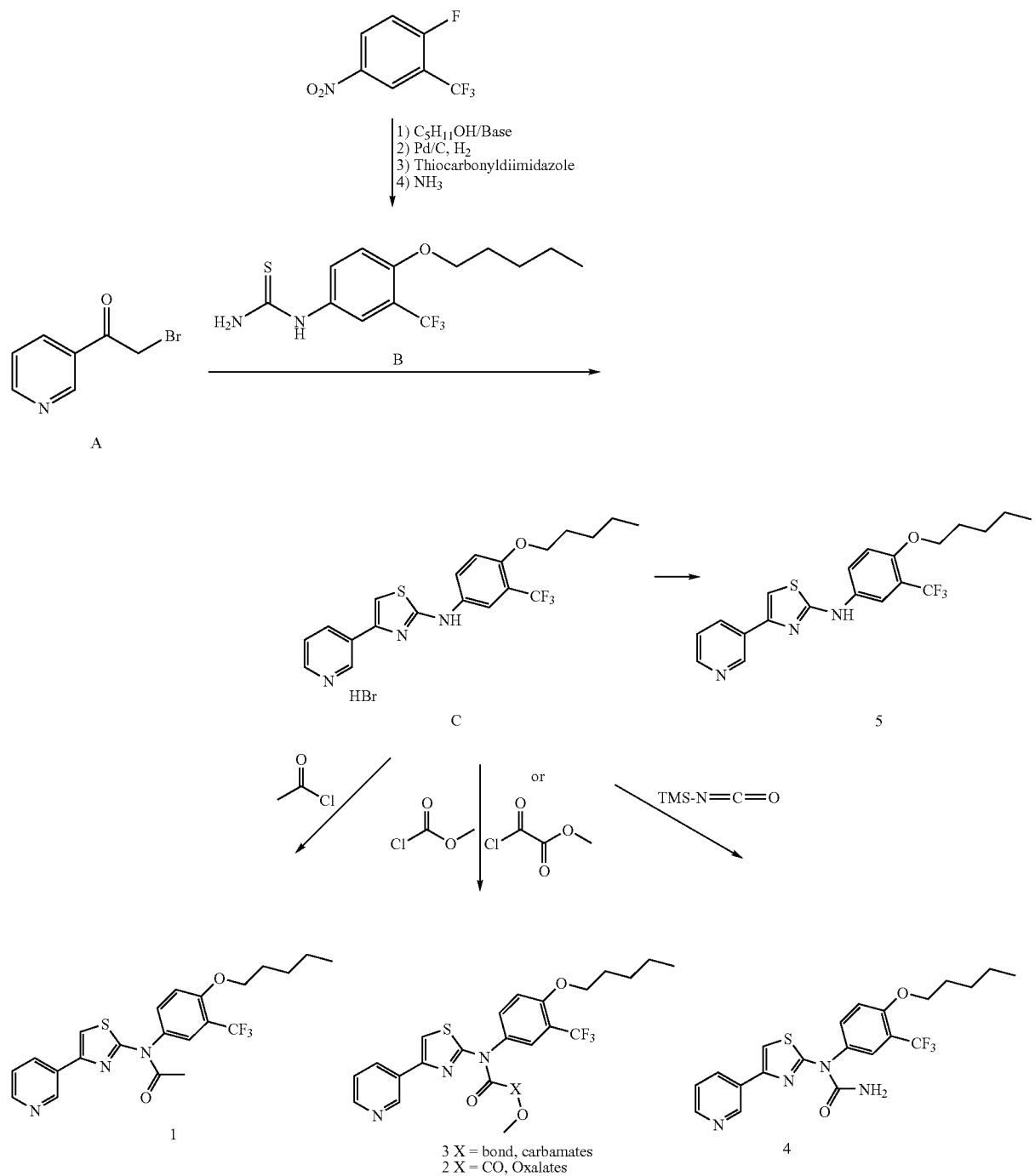

Compound C

3-Bromoacetylpyridine (A, 1 equivalent) and the thiourea B (1 equivalent) were heated between 50-70° C. in ethanol for 4-8 h. On cooling the reaction mixture a yellow solid precipitated. The solid was filtered and washed with minimum ethanol and dried to afford the amniothiazole (C) in 70% yield.

$^1$HNMR (CDCl$_3$) δ: 8.98 (d, 1H), 8.53 (dd, 1H), 8.06 (dt, 1H), 7.42 (s, 1H), 7.29 (dd, 1H), 7.13 (m, 1H), 7.03 (dd, 1H), 6.78 (d, 1H), 3.90 (t, 2H), 1.73 (m, 2H), 1.35 (m, 4H), 0.85 (t, 3H). MS: 408 (M$^+$+1).

Compounds 1, 2, 3

Compound C (1 equivalent) was treated with a slight excess of the corresponding acid chloride (acetyl chloride, methyloxalylchloride, methyl chloroformate) in Methylene chloride in presence of a base like pyridine or triethylamine. DMAP may also be added to the reaction. The reaction can also be done in Pyridine. The reaction was stirred at room temperature over night. The solvent was evaporated, residue suspended in water and extracted with methylene chloride, dried and evaporated. The residue was purified by crystallization or by column chromatography over silca gel or by preparative HPLC.

Compound 1

NMR (CDCl3) δ: 0.87 (t, 3H), 1.39 (m, 4H), 1.80 (m, 2H), 2.02 (s, 3H), 4.06 (t, 2H), 7.04 (d, 1H), 7.13 (dd, 1H), 7.19 (s, 1H), 7.38 (dd, 1H), 7.47 (brS, 1H), 7.78 (dt, 1H), 8.36 (d, 1H), 8.81 (s, 1H). MS: 450 (M$^+$+1)

Compound 2

$^1$HNMR (CDCl3) δ: 9.06 (d, 1H), 8.66 (dd, 1H), 8.40 (dd, 1H), 7.70 (dd, 1H), 7.52 (m, 2H), 7.61 (s, 1H), 7.08 (d, 1H), 4.09 (t, 2H), 3.62 (s, 3H), 1.82 (m, 2H), 1.40 (m, 4H), 0.83 (t, 3H).

Compound 3

$^1$HNMR (CDCl3) δ: 9.12 (s, 1H), 8.71 (d, 1H), 8.42 (dt, 1H), 7.78 (dd, 1H), 7.60 (s, 1H), 7.52 (d, 1H), 7.45 (dd, 1H), 7.13 (d, 1H), 4.15 (t, 2H), 3.87 (s, 3H), 1.95 (m, 2H), 1.50 (m, 4H), 1.04 (t, 3H) ppm. MS: 507 (M$^+$+1)

Compound 4

The aminothiazole C (1 equivalent) and trimethylsilyl isocynate (4 equivalent) were heated at 60° C. in THF overnight. The solvent was removed and the remaining residue was purified by HPLC to give 4.

$^1$HNMR (CDCl$_3$): 9.13 (d, 1H), 8.71 (dd, 1H), 8.42 (dt, 1H), 7.75 (dd, 1H), 7.64 (d, 1H), 7.57 (dd, 1H), 7.41 (s, 1H), 7.18 (d, 1H), 5.96 (s, 2H), 4.20 (t, 2H), 1.95 (m, 2H), 1.50 (m, 4H), 1.04 (t, 3H) ppm. MS: 451 (M$^+$+1)

Compound 5

The aminothiazole C (1 equivalent) and formaldehyde and acetic anhydride were heated at 60° C. overnight. The solvent was removed and the remaining residue was purified by HPLC to give 5.

$^1$HNMR (CDCl$_3$): 9.16 (s, 1H), 8.72 (2H), 8.45 (d, 1H), 7.73 (m, 1H), 7.61 (d-like, 3H), 7.21 (d, 1H), 4.20 (t, 2H), 1.95 (m, 2H), 1.50 (m, 4H), 1.04 (t, 3H) ppm. MS: 436 (M$^+$+1)

Compounds 6 and 7

Thiazole carboxylic acid and chloromethylene thiazole were prepared by reacting the corresponding bromoketones with thiourea as shown in schemes 2 and 3 following procedure described for compound C. The acids were then converted to the corresponding amides following standard conditions. The chloromethylene thiazoles were reacted with different amines in presence of a base in DMF followed by purification by HPLC to afford the amino compounds. These were derivatized as described above.

Compound 6:

MS: 430 (M$^+$+1)

Compound 7:

$^1$H NMR (CDCl$_3$) δ: 9.11 (s, 1H), 9.05 (s, 1H), 8.6 (d, 1H), 8.46 (d, 1H), 8.09 (s, 1H), 7.7 (m, 2H), 7.53 (d, 1H), 7.11 (d, 1H), 4.09 (t, 2H), 3.62 (s, 3H), 1.82 (m, 2H), 1.39 (m, 4H)

Example 2

Synthesis of 5-fluoro-N-(4-octyl-3-(trifluoromethyl) phenyl)-4-(pyridin-3-yl)thiazol-2-amine

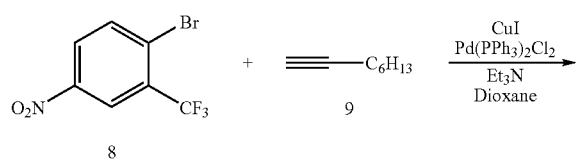

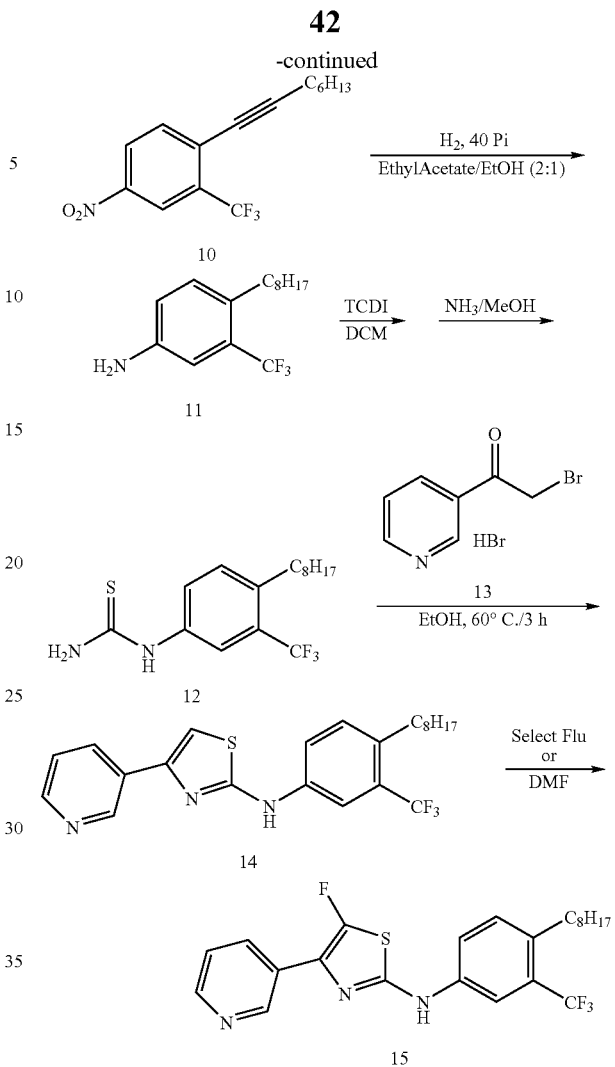

Step 1. Preparation of 4-nitro-1-(oct-1-ynyl)-2-(trifluoromethyl)benzene

A mixture of 1 (1-Bromo-4-nitro-2-trifluoromethyl-benzene, 10.8 g, 40 mmol), 2 (Oct-1-yne, 6.6 g, 60 mmol), CuI (1.52 g, 8 mmol), Pd(PPh$_3$)$_2$Cl$_2$ (1.8 g), Et$_3$N (22 ml, 160 mmol), and dioxane (22 ml) in a sealed tube under Ar is heated at 100° C. for 16 h. After cooling to rt, the mixture is filtered through celite, and washed with ethyl acetate. The filtrate is concentrated and passed over silica gel column (Ethyl acetate:Hexane=1:7) to remove baseline impurities to give crude 10 as an oil.

Step 2. Preparation of 4-octyl-3-(trifluoromethyl)aniline

The crude 10 is dissolved in a mixture of ethyl acetate and ethanol (40 ml/20 ml). 10% Pd/C (1 g) is added and the mixture hydrogenated under 40 psi at rt for 16 h. The mixture is filtered through celite and washed with ethyl acetate. The filtrate is concentrated to give crude 11 (10.6 g).

Step 3. 1-(4-octyl-3-(trifluoromethyl)phenyl)thiourea

A solution of crude 11 (10.6 g) in anhydrous CH$_2$Cl$_2$ (50 ml) at 0° C. is added drop wise to a solution of TCDI (14 g, 78 mmol) in anhydrous CH$_2$Cl$_2$ (250 ml). After addition, the mixture is warmed to rt and stirred for 3 h. The mixture is cooled to 0° C. and ammonia (7N in MeOH, 50 ml) was added drop wise. After addition, the mixture is allowed to warm to rt and stirred for 16 h. After concentration, water (300 ml) is added and stirred for 1 h and the solid is filtered and washed with water. The desired product 12 is dried in vacuum to give a white solid (11 g).

Step 4. Preparation of N-(4-octyl-3-(trifluoromethyl) phenyl)-4-(pyridin-3-yl)thiazol-2-amine A mixture of 5 (13.3 g, 40 mmol) and 13 (12.36 g, 44 mmol) in ethanol (200 ml) is heated at 60° C. for 3 h. The reaction is cooled and the pH was adjusted to pH=7~8, with concentrated ammonium hydroxide followed by addition of water (200 ml). The solid is collected by filtration and recrystallized from ethanol to give 13.3 g of 14.

Step 5. Preparation of Final Product

To a solution of 14 (6.5, 15 mmol) in anhydrous DMF (60 ml) at 0° C. was added SelectFlour (5.32 g, 15 mmol) in one portion, the mixture was slowly warmed to rt in 2 h and stirred for additional 24 h. A NH$_3$/MeOH-solution and H$_2$O was added while rapidly stirring and stirring continued for 48 hours. After water (60 ml) was added, the solid was filtered off and dried, purified by silica gel column chromatography (Ethyl acetate/Hexane=1:1) to give the desired product as a off-white solid: 3.5 g (~50% yield).

Example 3

Preparation of Compound 13
(Reactant in Example 3)

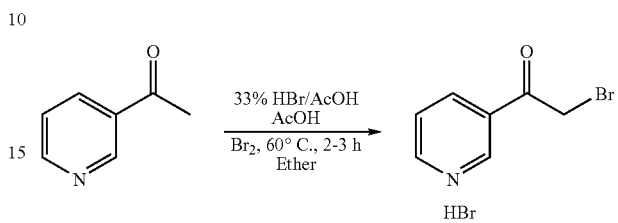

Acetylpyridine (120 g) is added to 33% HBr/AcOH (600 ml) with stirring (If the salt precipitates more AcOH, up to 800 ml may be added). Bromine (176 g) is added and the reaction mixture is heated to 60° C. for 2-3 h. The reaction mixture is cooled and ether (1400 ml) is added. The solid is filtered, washed with ether, and dried to give 2-bromo-1-(pyridin-3-yl)ethanone hydrobromide (Compound 13), in quantitative yield Example 4

Synthesis of Prodrugs

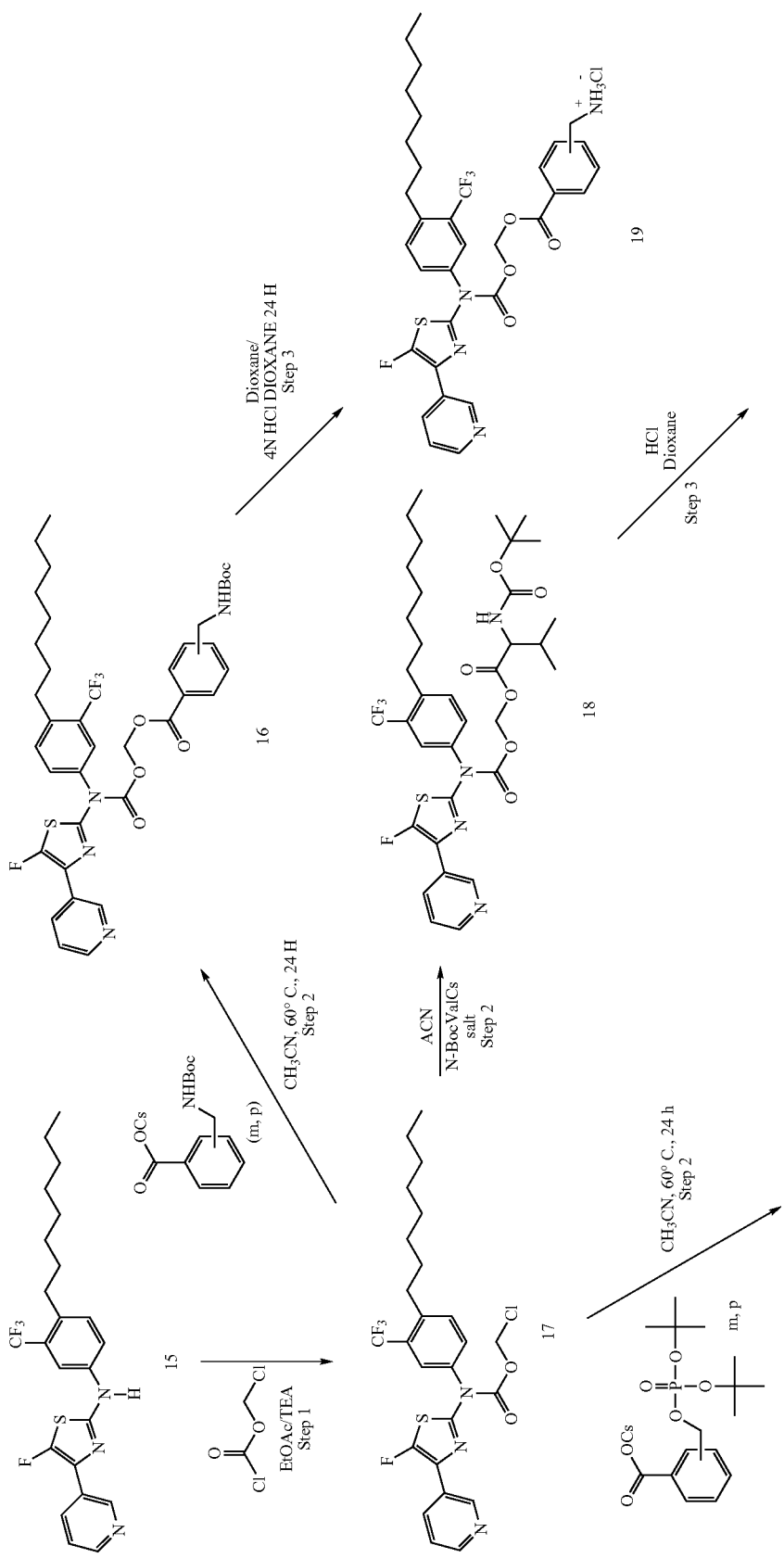

-continued
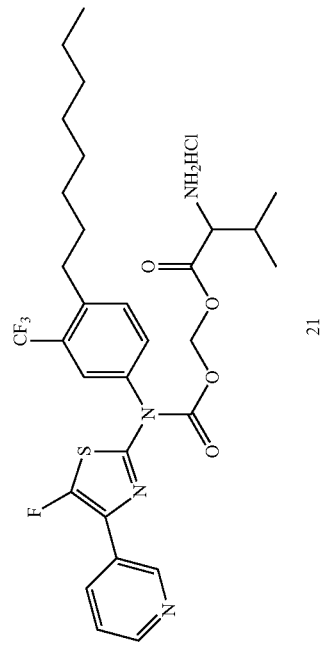
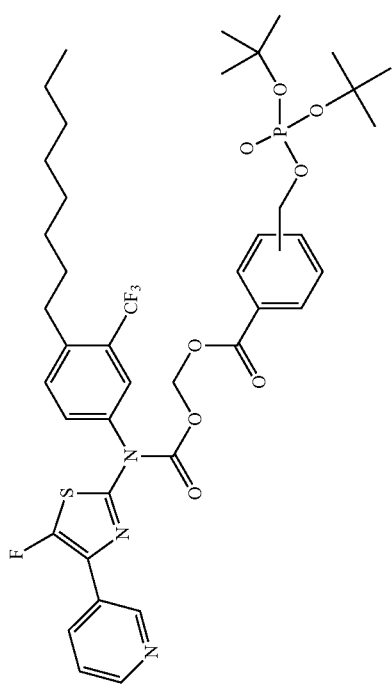
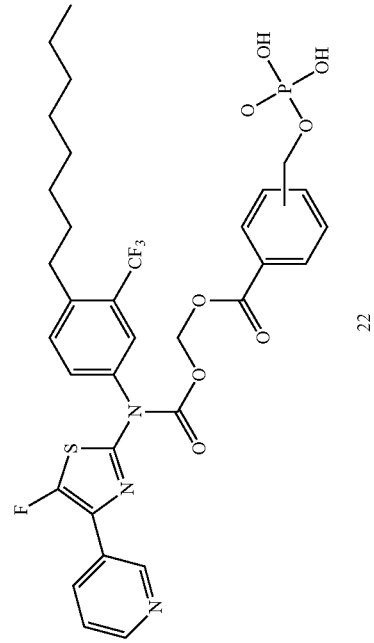

Step 1. Preparation of Chloromethyl 5-fluoro-4-(pyridin-3-yl)thiazol-2-yl(4-octyl-3-(trifluoromethyl)phenyl)carbamate (17)

Compound 15 (21 gm, 48 mmol) is dissolved in ethyl acetate (700 ml) at 0° C. TEA 52.8 mmol, 4.693 ml) and chloromethyl chloroformate (52.8 mmol, 7.728 mmol) are added, and the resulting reaction mixture is stirred overnight. After reaction completion (monitored by TLC and LCMS) solvent is washed with water and 5% NaHCO$_3$ solution. The organic layer is separated, dried, and evaporated using reduced pressure. The crude product is purified by column chromatography afforded 23.5 gm (90%).

Step 2. Protection (Formation of cmpd. 18)

Reaction of Cesium salt: SM-1 (1 mmol) is dissolved in acetonitrile. Cesium salt of acid (1 mmol) is added and the reaction mixture is stirred at 60° C. for 24 h. After reaction completion of the reaction (monitored by LCMS) solvent is removed and diluted with ethyl acetate, washed with water, dried, and concentrated. The product is purified by chromatography over silica gel using EtOAc/DCM. Yield ~60-70%.

Step 3. Deprotection (Formation of cmpd. 21)

SM(~400 mg) is dissolved in 1,4-dioxane (4 ml). At 0° C., 4N HCl in Dioxane (4 ml) is added, the reaction mixture is stirred at RT for 12 h-24 h. After completion, the reaction (monitored by LCMS) solvent is removed and the residue washed with ether to afford the HCl salt of the corresponding prodrug as a white solid, yield ~95%.

Step 4. Deprotection (Formation of cmpd. 22)

SM is dissolved in TFA/DCM (2 ml+2 ml); the reaction mixture is stirred at RT for 2 h. After completion, the reaction (monitored by LCMS) solvent is removed and the residue washed with ether to afford the TFA salt of the corresponding prodrug as a white solid. Yield 70-80%.

Example 5

Additional Prodrugs

TABLE A

| ACH | Structure | Name | Rat (30 mg/kg dose) $C_{max}$ (ng/ml) | Rat AUC (h*ng/ml) | Dog (10 mg/kg dose) $C_{max}$ (ng/ml) | Dog AUC (h*ng/ml) |
|---|---|---|---|---|---|---|
| 23 | | 2-(dimethylamino)ethyl 5-fluoro-4-(pyridin-3-yl)thiazol-2-yl(4-octyl-3-(trifluoromethyl)phenyl)carbamate, iodide salt | | | | |
| 24 | | 2-(trimethylamino)ethyl 5-fluoro-4-(pyridin-3-yl)thiazol-2-yl(4-octyl-3-(trifluoromethyl)phenyl)carbamate, iodide salt | | | | |
| 25 | | 4-(((5-fluoro-4-(pyridin-3-yl)thiazol-2-yl)(4-octyl-3-(trifluoromethyl)phenyl)amino)methyl)-5-methyl-1,3-dioxol-2-one | + | + | | |
| 26 | | 2-((5-fluoro-4-(pyridin-3-yl)thiazol-2-yl)(4-octyl-3-(trifluoromethyl)phenyl)carbamoyl) benzyl dihydrogen phosphate | BLQ | BLQ | | |

TABLE A-continued

| ACH | Structure | Name | Rat (30 mg/kg dose) | | Dog (10 mg/kg dose) | |
|---|---|---|---|---|---|---|
| | | | C$_{max}$ (ng/ml) | AUC (h*ng/ml) | C$_{max}$ (ng/ml) | AUC (h*ng/ml) |
| 27 | 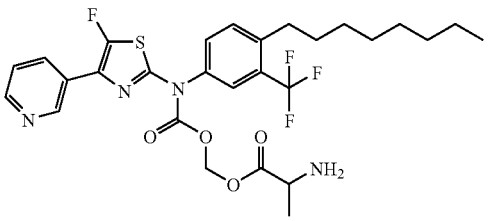 | ((5-fluoro-4-(pyridin-3-yl)thiazol-2-yl)(4-octyl-3-(trifluoromethyl)phenyl)carbamoyl-oxy)methyl 2-aminopropanoate | +++ | +++ | | |
| 28 | 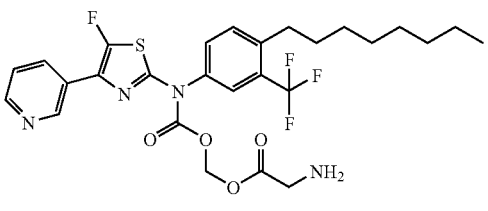 | ((5-fluoro-4-(pyridin-3-yl)thiazol-2-yl)(4-octyl-3-(trifluoromethyl)phenyl)carbamoyl-oxy)methyl 2-aminoacetate | +++ | +++ | | |
| 29 | 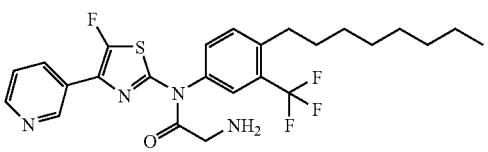 | 2-amino-N-(5-fluoro-4-(pyridin-3-yl)thiazol-2-yl)-N-(4-octyl-3-(trifluoromethyl)phenyl)acetamide | ++ | ++ | | |
| 30 | 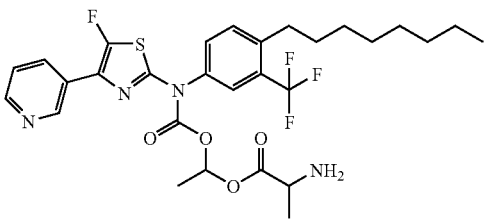 | 1-((5-fluoro-4-(pyridin-3-yl)thiazol-2-yl)(4-octyl-3-(trifluoromethyl)phenyl)carbamoyl-oxy)ethyl 2-aminopropanoate | +++ | +++ | | |
| 31 | 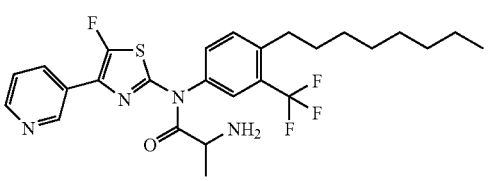 | 2-amino-N-(5-fluoro-4-(pyridin-3-yl)thiazol-2-yl)-N-(4-octyl-3-(trifluoromethyl)phenyl)propanamide | | | | |
| 32 | 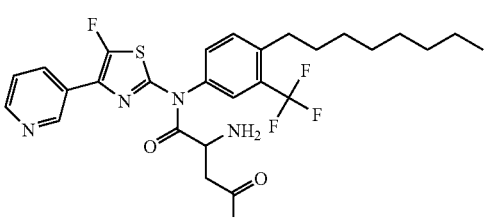 | 3-amino-4-((5-fluoro-4-(pyridin-3-yl)thiazol-2-yl)(4-octyl-3-(trifluoromethyl)phenyl)amino)-4-oxobutanoic acid | | | | |

TABLE A-continued

| ACH | Structure | Name | Rat (30 mg/kg dose) | | Dog (10 mg/kg dose) | |
| --- | --- | --- | --- | --- | --- | --- |
| | | | $C_{max}$ (ng/ml) | AUC (h*ng/ml) | $C_{max}$ (ng/ml) | AUC (h*ng/ml) |
| 33 | 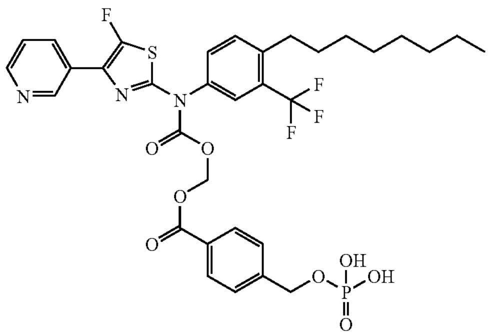 | ((5-fluoro-4-(pyridin-3-yl)thiazol-2-yl)(4-octyl-3-(trifluoromethyl)phenyl)carbamoyl-oxy)methyl 4-(phosphonooxymethyl)benzoate | +++ | +++ | ++ | +++ |
| 34 | 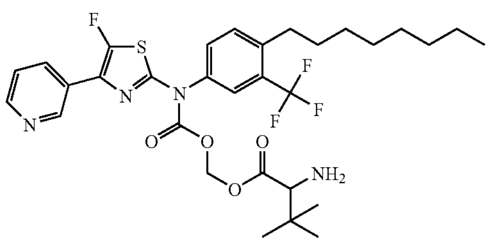 | ((5-fluoro-4-(pyridin-3-yl)thiazol-2-yl)(4-octyl-3-(trifluoromethyl)phenyl)carbamoyl-oxy)methyl 2-amino-3,3-dimethylbutanoate | +++ | +++ | | |
| 35 | 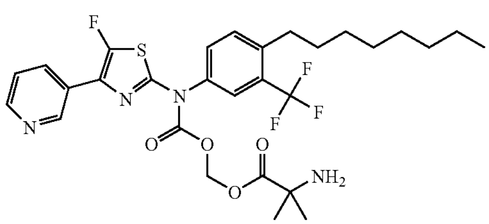 | ((5-fluoro-4-(pyridin-3-yl)thiazol-2-yl)(4-octyl-3-(trifluoromethyl)phenyl)carbamoyl-oxy)methyl 2-amino-2-methylpropanoate | | | | |
| 36 | 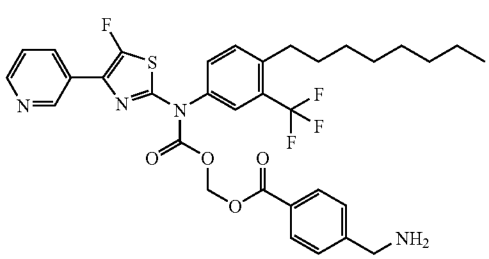 | ((5-fluoro-4-(pyridin-3-yl)thiazol-2-yl)(4-octyl-3-(trifluoromethyl)phenyl)carbamoyl-oxy)methyl 4-(aminomethyl)benzoate | +++ | +++ | +++ | +++ |
| 37 | 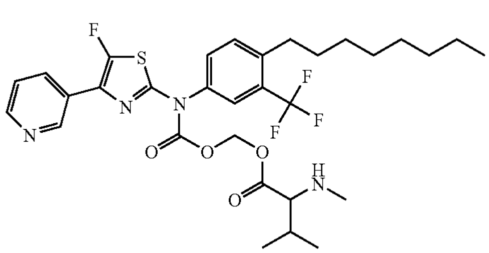 | ((5-fluoro-4-(pyridin-3-yl)thiazol-2-yl)(4-octyl-3-(trifluoromethyl)phenyl)carbamoyl-oxy)methyl 3-methyl-2-(methylamino)butanoate | +++ | +++ | | |

TABLE A-continued

| ACH | Structure | Name | Rat (30 mg/kg dose) | | Dog (10 mg/kg dose) | |
|---|---|---|---|---|---|---|
| | | | $C_{max}$ (ng/ml) | AUC (h*ng/ml) | $C_{max}$ (ng/ml) | AUC (h*ng/ml) |
| 38 | 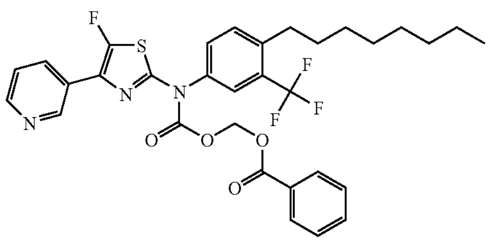 | ((5-fluoro-4-(pyridin-3-yl)thiazol-2-yl)(4-octyl-3-(trifluoromethyl)phenyl)carbamoyl-oxy)methyl benzoate | + | ++ | | |
| 39 | 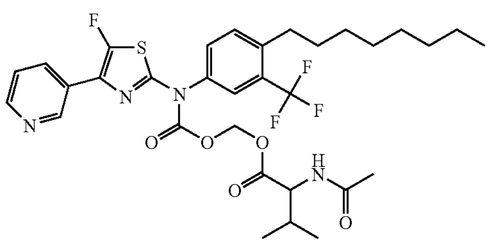 | ((5-fluoro-4-(pyridin-3-yl)thiazol-2-yl)(4-octyl-3-(trifluoromethyl)phenyl)carbamoyl-oxy)methyl 2-acetamido-3-methylbutanoate | ++ | +++ | +++ | +++ |
| 40 | 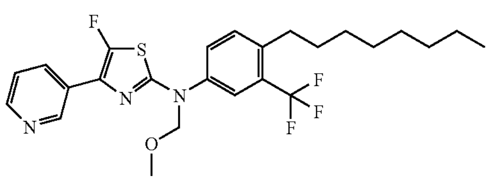 | 5-fluoro-N-(methoxymethyl)-N-(4-octyl-3-(trifluoromethyl)phenyl)-4-(pyridin-3-yl)thiazol-2-amine | | | + | ++ |
| 41 | 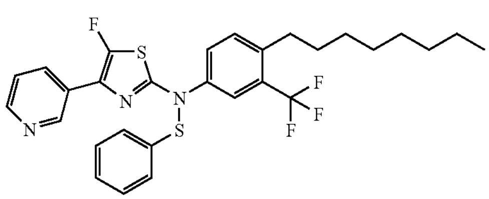 | N-(5-fluoro-4-(pyridin-3-yl)thiazol-2-yl)-N-(4-octyl-3-(trifluoromethyl)phenyl)-S-phenylthiohydroxylamine | | | | |
| 42 | 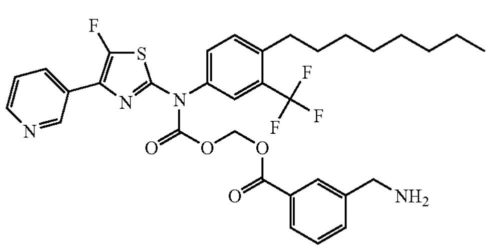 | ((5-fluoro-4-(pyridin-3-yl)thiazol-2-yl)(4-octyl-3-(trifluoromethyl)phenyl)carbamoyl-oxy)methyl 3-(aminomethyl)benzoate | | | +++ | +++ |
| 43 | 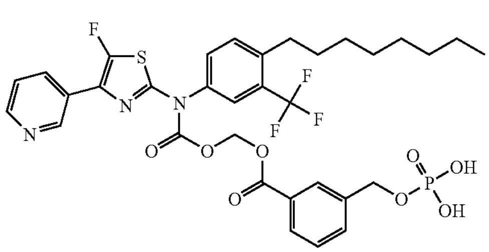 | ((5-fluoro-4-(pyridin-3-yl)thiazol-2-yl)(4-octyl-3-(trifluoromethyl)phenyl)carbamoyl-oxy)methyl 3-(phosphonooxymethyl)benzoate | | | +++ | +++ |

TABLE A-continued

| ACH | Structure | Name | Rat (30 mg/kg dose) | | Dog (10 mg/kg dose) | |
|---|---|---|---|---|---|---|
| | | | $C_{max}$ (ng/ml) | AUC (h*ng/ml) | $C_{max}$ (ng/ml) | AUC (h*ng/ml) |
| 44 | 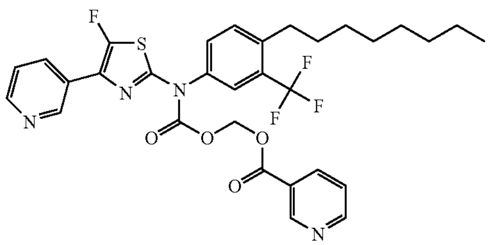 | ((5-fluoro-4-(pyridin-3-yl)thiazol-2-yl)(4-octyl-3-(trifluoromethyl)phenyl)carbamoyl-oxy)methyl nicotinate | | | +++ | +++ |
| 45 | 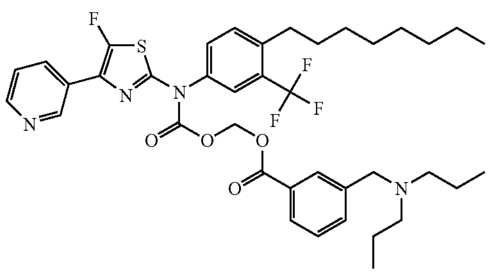 | ((5-fluoro-4-(pyridin-3-yl)thiazol-2-yl)(4-octyl-3-(trifluoromethyl)phenyl)carbamoyl-oxy)methyl 3-((dipropylamino)methyl)benzoate | | | +++ | +++ |
| 46 | 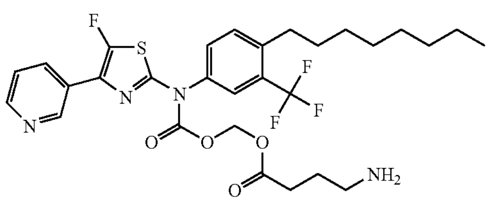 | ((5-fluoro-4-(pyridin-3-yl)thiazol-2-yl)(4-octyl-3-(trifluoromethyl)phenyl)carbamoyl-oxy)methyl 4-aminobutanoate | | | +++ | +++ |
| 47 | 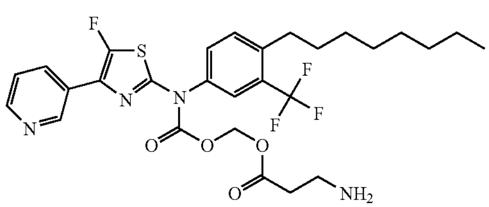 | ((5-fluoro-4-(pyridin-3-yl)thiazol-2-yl)(4-octyl-3-(trifluoromethyl)phenyl)carbamoyl-oxy)methyl 3-aminopropanoate | | | +++ | +++ |
| 48 | 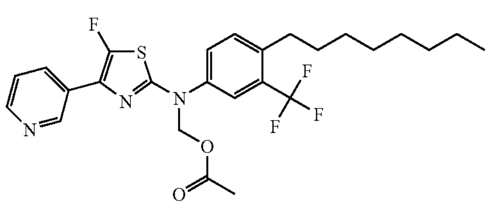 | ((5-fluoro-4-(pyridin-3-yl)thiazol-2-yl)(4-octyl-3-(trifluoromethyl)phenyl)amino)-methyl acetate | | | +++ | +++ |
| 49 | 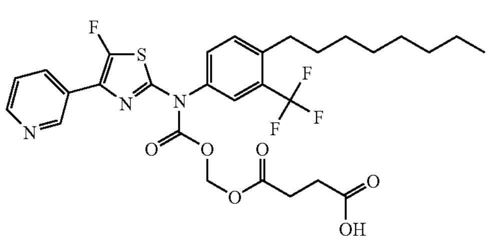 | 4-(((5-fluoro-4-(pyridin-3-yl)thiazol-2-yl)(4-octyl-3-(trifluoromethyl)phenyl)carbamoyl-oxy)methoxy)-4-oxobutanoic acid | | | +++ | +++ |

TABLE A-continued

| ACH | Structure | Name | Rat (30 mg/kg dose) $C_{max}$ (ng/ml) | Rat (30 mg/kg dose) AUC (h*ng/ml) | Dog (10 mg/kg dose) $C_{max}$ (ng/ml) | Dog (10 mg/kg dose) AUC (h*ng/ml) |
|---|---|---|---|---|---|---|
| 50 | (structure) | ((5-fluoro-4-(pyridin-3-yl)thiazol-2-yl)(4-octyl-3-(trifluoromethyl)phenyl)carbamoyloxy)methyl acetate | | | +++ | +++ |
| 51 | (structure) | 3-(((((5-fluoro-4-(pyridin-3-yl)thiazol-2-yl)(4-octyl-3-(trifluoromethyl)phenyl)carbamoyloxy)methoxy)carbonyl)benzoic acid | | | | |
| 52 | (structure) | ((5-fluoro-4-(pyridin-3-yl)thiazol-2-yl)(4-octyl-3-(trifluoromethyl)phenyl)carbamoyloxy)methyl pivalate | | | | |
| 53 | (structure) | ((5-fluoro-4-(pyridin-3-yl)thiazol-2-yl)(4-octyl-3-(trifluoromethyl)phenyl)carbamoyloxy)methyl isobutyrate | | | | |
| 54 | (structure) | ((5-fluoro-4-(pyridin-3-yl)thiazol-2-yl)(4-octyl-3-(trifluoromethyl)phenyl)carbamoyloxy)methyl 1-(tert-butoxycarbonylamino)cyclopropanecarboxylate | | | | |
| 55 | (structure) | ((5-fluoro-4-(pyridin-3-yl)thiazol-2-yl)(4-octyl-3-(trifluoromethyl)phenyl)carbamoyloxy)methyl 1-aminocyclopropanecarboxylate | | | | |

$C_{max}$ Scale: + = 1-99 ng/ml, ++ = 100-999 ng/ml, +++ > 1000 ng/ml

AUC Scale: + = 1-99 h*ng/ml, ++ = 100-999 h*ng/ml, +++ > 1000 h*ng/ml

The compounds shown below in may be synthesized by the methods given in Examples 1 to 4, and by variations in the methods disclosed in these examples and that will be readily apparent to those of skill in the art of synthetic organic synthesis.

The arrays provided below show disclose compounds of the general formula

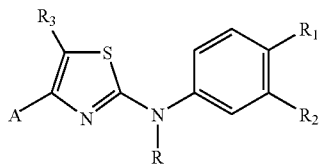

The values for "A" in this formula are found in Array A.

The values for "R" in this formula are found in Array R; the values for "$R_3$" are given in Array $R_3$, the values for "$R_1$" and "$R_2$" are given in Array L and Array M where one of $R_1$ and $R_2$ is L and the other is M.

Each combination of 1 element from each of Array A, Array R, Array $R_3$, Array L, and Array M specifically discloses two discrete compounds of the invention.

For example [A-1][R-2][$R_3$-3][L-7][M-8] denotes the following two discrete compounds:

Compound A

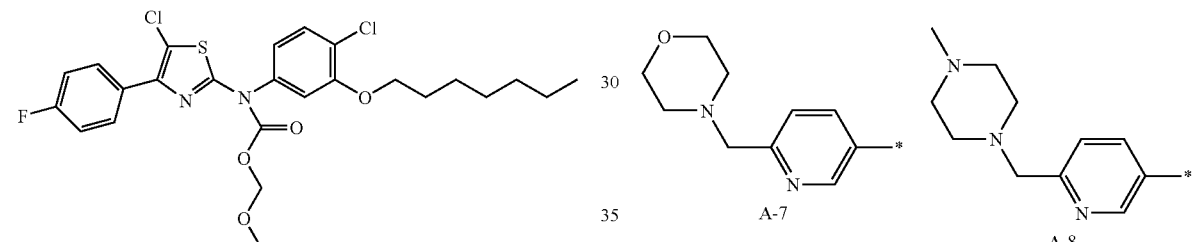

Compound B

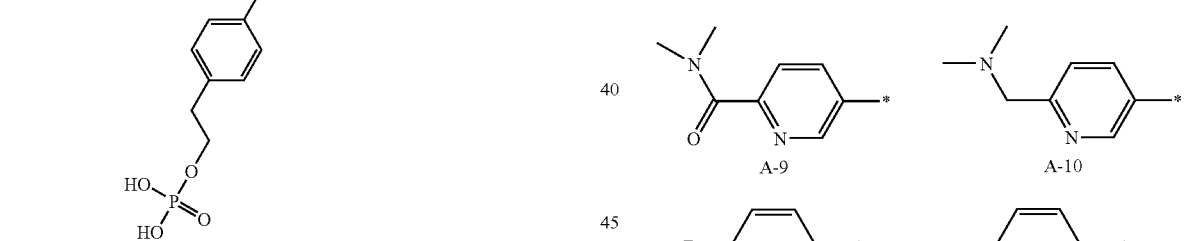

When the positions of the Array L and Array M elements are specified each combination of 1 element from each of Array A, Array R, Array $R_3$, Array L, and Array M specifically discloses one discrete compound of the invention. For example [A-1][R-2][$R_3$-3][L-7](L=$R_1$)[M-8](M=$R_2$) denotes Compound A above.

| ARRAY A |
|---|

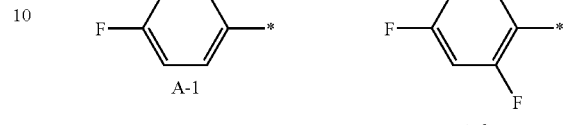

A-1, A-2

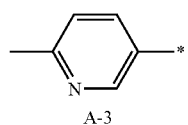

A-3, A-4

A-5, A-6

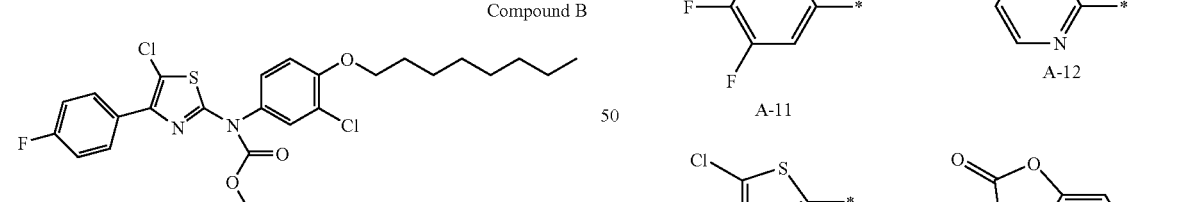

A-7, A-8

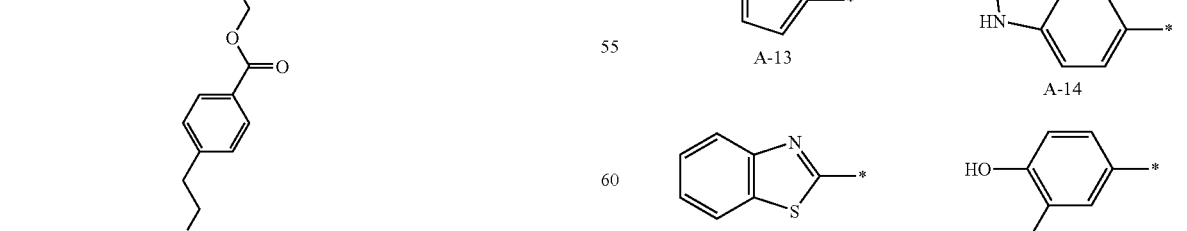

A-9, A-10

A-11, A-12

A-13, A-14

A-15, A-16

ARRAY A
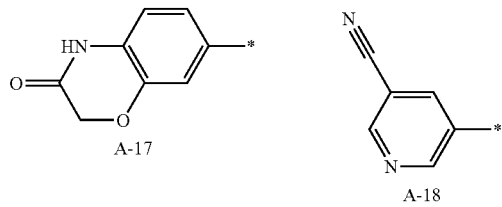
A-17, A-18
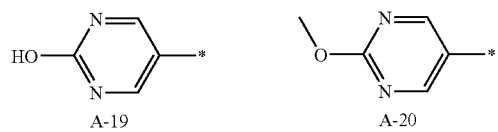
A-19, A-20
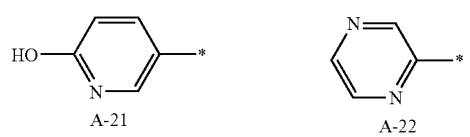
A-21, A-22
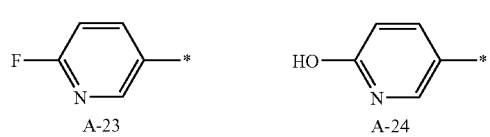
A-23, A-24
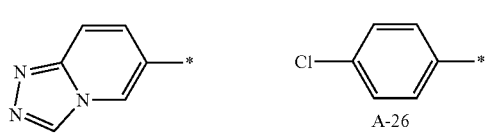
A-25, A-26
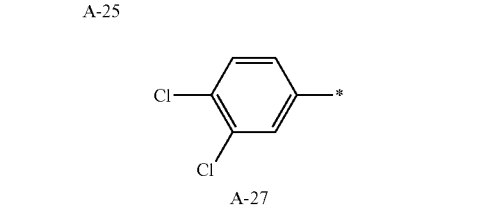
A-27
ARRAY R
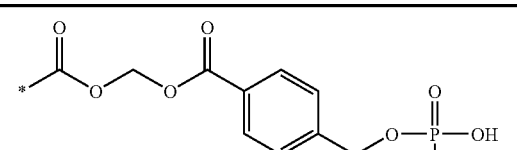
R-1
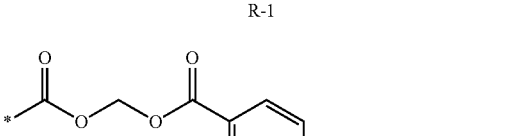
R-2
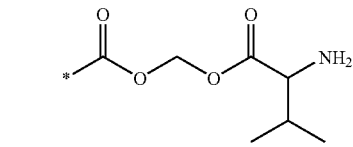
R-3
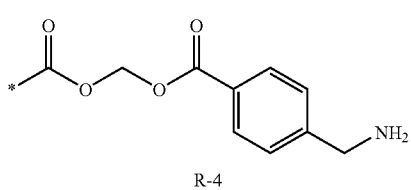
R-4
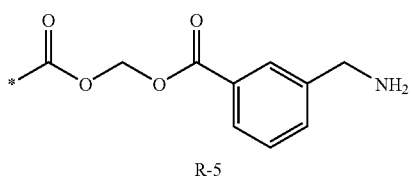
R-5
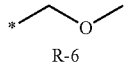
R-6
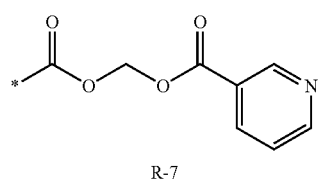
R-7
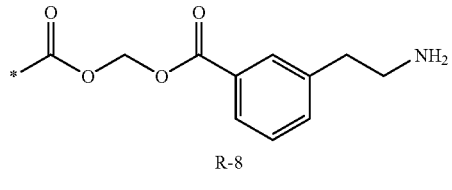
R-8
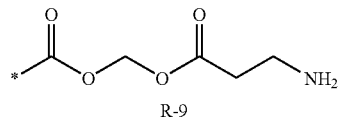
R-9
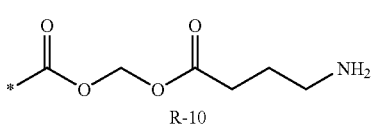
R-10

-continued
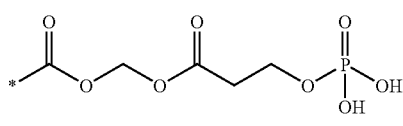
R-11
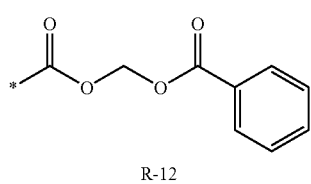
R-12
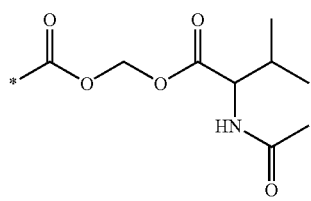
R-13
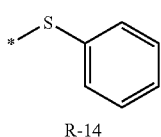
R-14
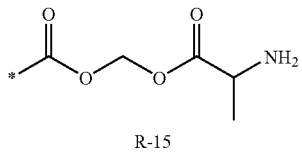
R-15
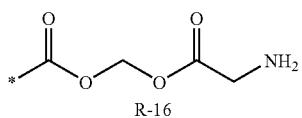
R-16
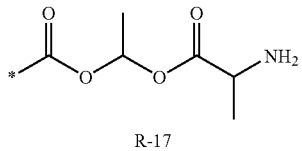
R-17
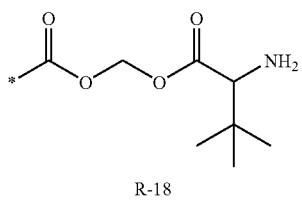
R-18
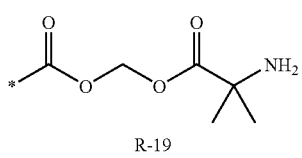
R-19
-continued
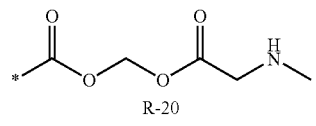
R-20
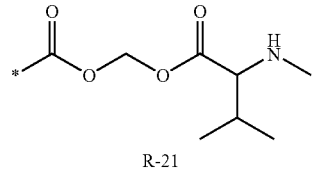
R-21
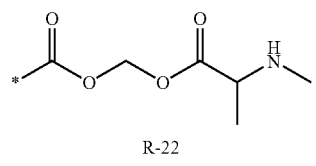
R-22
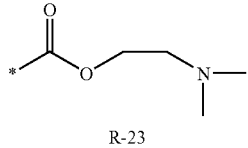
R-23
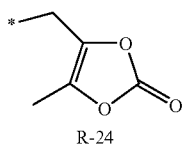
R-24
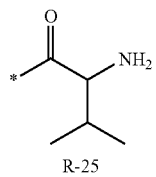
R-25
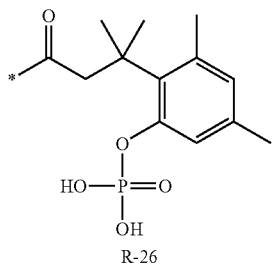
R-26
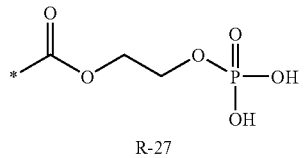
R-27
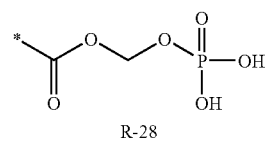
R-28

-continued
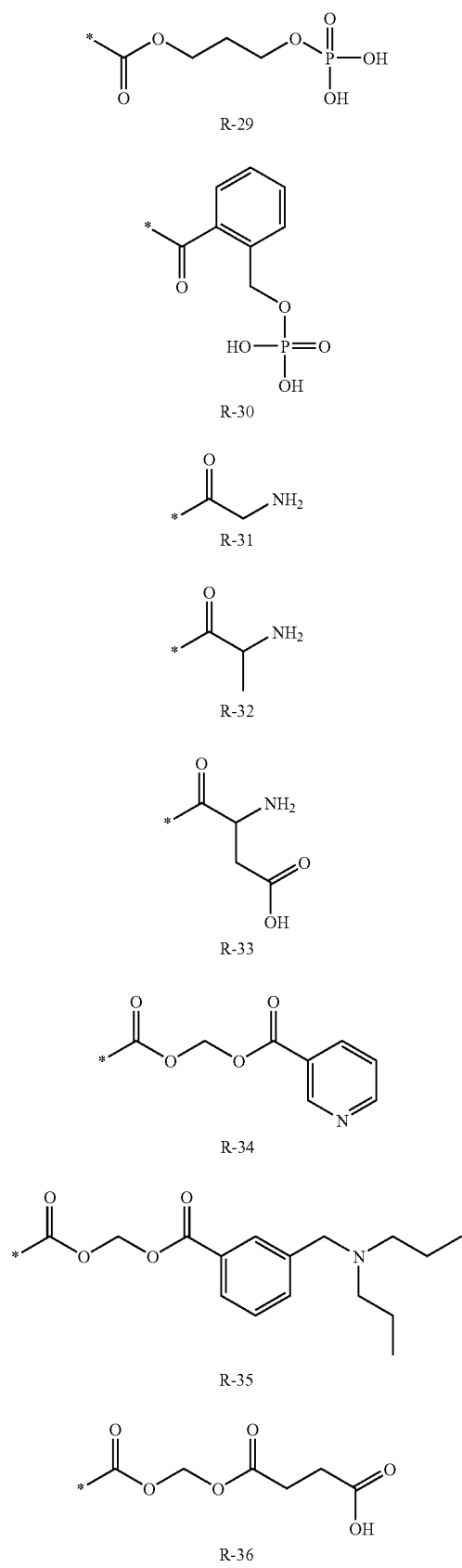
-continued
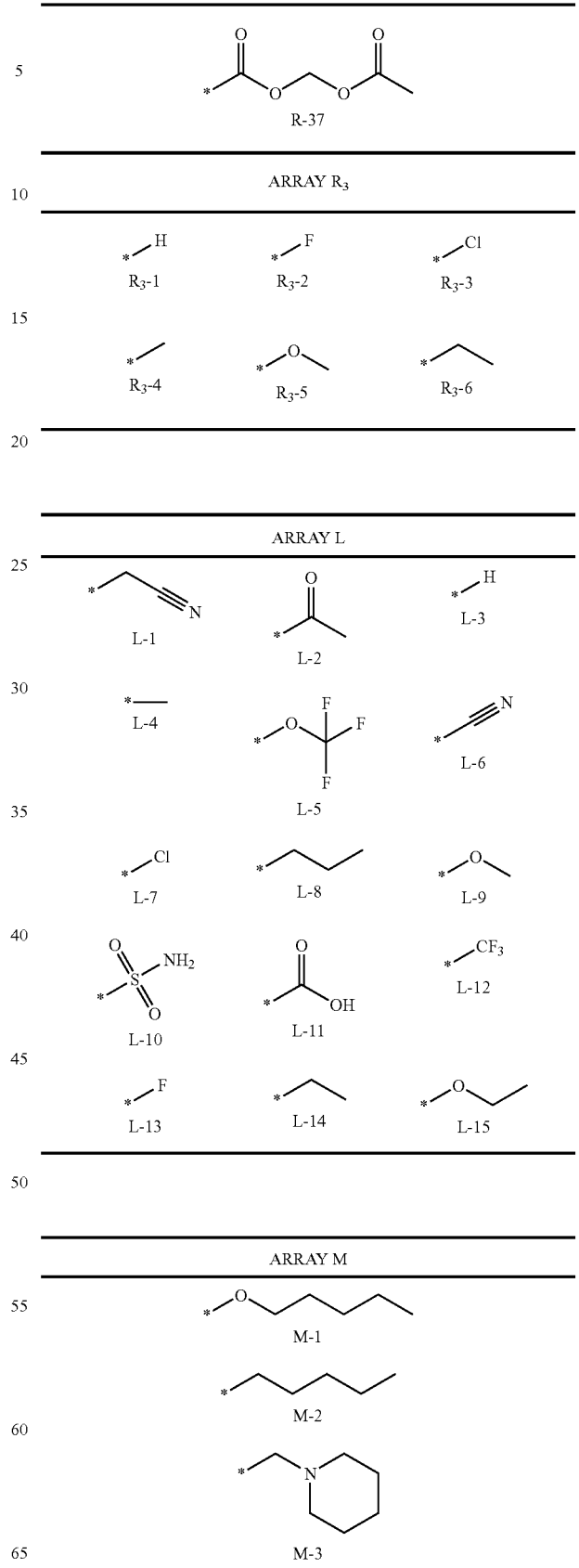

ARRAY M
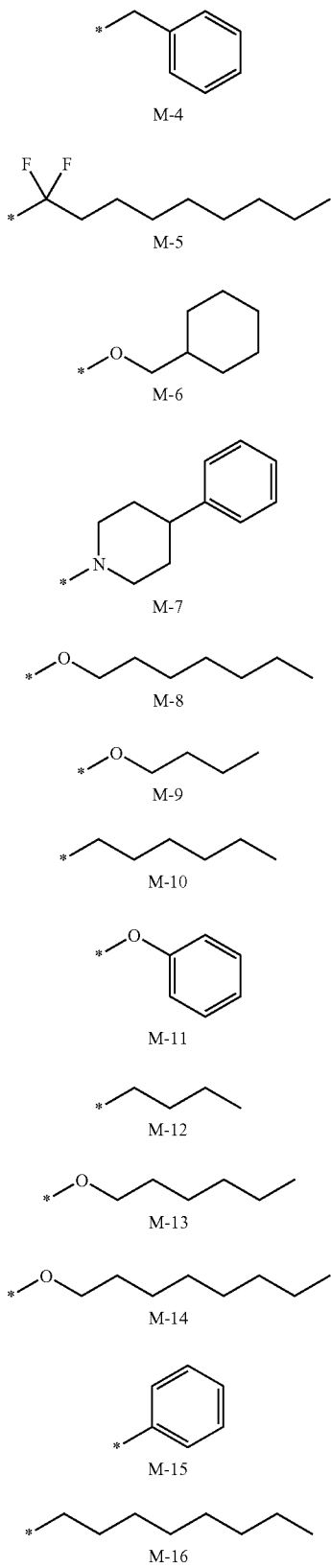
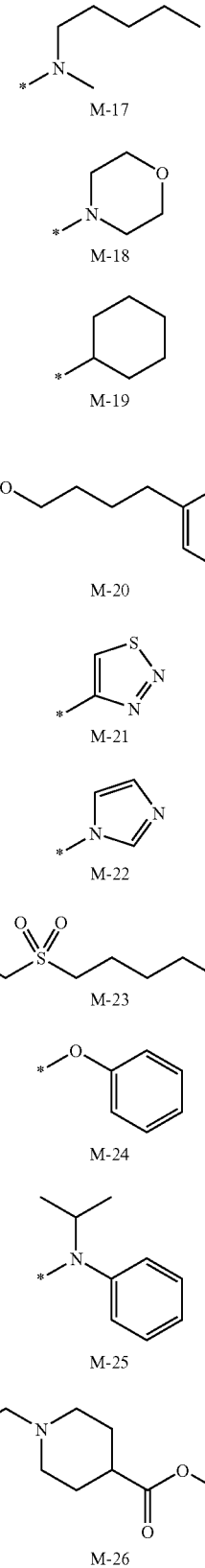

ARRAY M

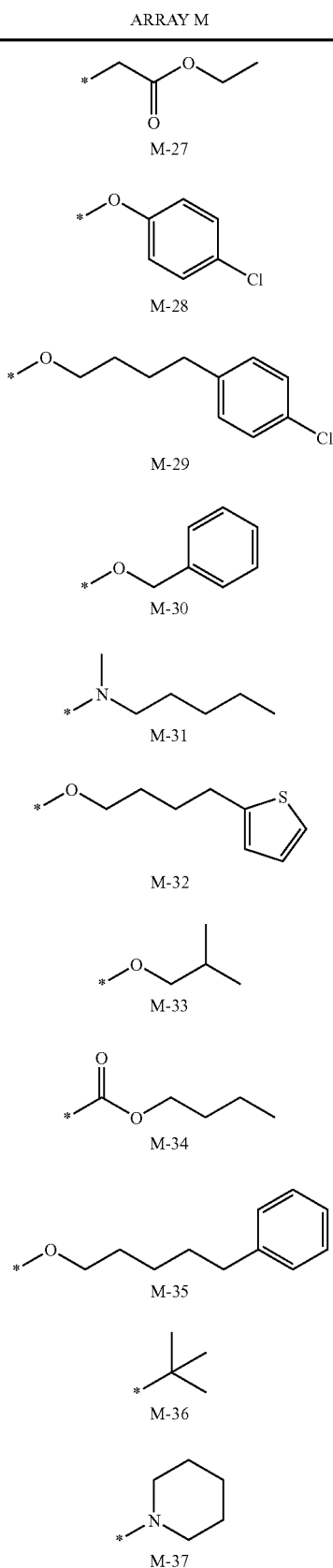

M-27, M-28, M-29, M-30, M-31, M-32, M-33, M-34, M-35, M-36, M-37

Example 6

In Vivo Pharmacokinetic Studies

A. Dose Formulation Vehicles

Selection of the appropriate vehicle for each prodrug is based on the stability and solubility of the prodrug in the formulation. For all studies a clear (i.e. soluble) formulation is obtained for dosing prodrugs. Exemplary prodrug vehicles are 0.5% methylcellulose- or water-based formulations with prodrug-specific modifications for pH and/or solubility. The more lipophilic prodrugs are formulated in polyethylene glycol-based vehicles modified with substances including, but not limited to, polypropylene glycol, TPGS, ethanol, and labrosol.

B. Screening in Rats

Prodrug pharmacokinetic screening in male Sprague Dawley rats (n=3) is performed by administering a single 30-mg/kg dose by oral gavage at a dose volume of 5 mL/kg to a non-fasted rat. Blood samples are obtained at 0.5, 1, 2, 4, and 6 hr post dose. Plasma obtained at each of these time points is analyzed by LC-MS/MS as described below.

C. Screening in Dogs

Prodrug screening in male Beagle dogs (n=3) is performed by administering a single 10-mg/kg dose by oral gavage at a dose volume of 5 mL/kg to a fed dog. Blood samples are obtained at predose, 0.25, 0.5, 1, 2, 4, 6, 8, 12, 24, and 48 hr post dose. Plasma obtained at each of these time points is analyzed by LC-MS/MS as described below.

D. Bioanalytical Methodology

Plasma is analyzed by LC-MS/MS using multiple reaction monitoring. A Deuterium-labeled non-prodrug aryl substituted aminothiazole is utilized as the internal standard. Each analysis run includes calibration standards and quality control samples. Calibration standards are within 30% of nominal or are excluded from the analysis. Noncompartmental pharmacokinetics are performed on individual animal data using WinNonlin. Pharmacokinetic parameters are reported as the mean value for each dose group.

Example 7

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et. al (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

7A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.

7B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin (G418), screening media (DMEM supplemented with 10% FBS, L-glutamine, non-essential amino acids, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu-N11, and enhancement solution.

HCV replicon-containing cells support high levels of viral RNA replicon replication when their density is suitable. Over-confluency causes decreased viral RNA replication. Therefore, cells must be kept growing in log phase in the presence of 500 micrograms/ml of G418. Generally, cells should be passed twice a week at 1:4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well (6-7.5×$10^5$ cells/10 ml/plate). The plates are then incubated at 37° C. in a 5% $CO_2$ incubator.

Cells are examined under a microscope approximated 24 hours after seeding and prior to adding drugs. If counting and dilution were performed correctly, cells are 60-70% confluent and nearly all cells should attach and spread evenly in the well.

7C. Treatment of HCV-Replicon Containing Cells with Test Compound

HCV replicon-containing cells are rinsed with once PBS once; 2 mls of trypsin are then added. Cells are incubated at 37° C. in a 5% $CO_2$ incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL catalog #10131-035), 5 ml MEM non-essential amino acids (100×BRL #11140-050) and 5 ml pen-strep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 cells/100 µl/well of 96 well plate (6-7.5×$10^5$ cells/10 ml/plate). Plates are placed into 37° C. 5% $CO_2$ incubator overnight.

7D. Assay

The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 µl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% $CO_2$ environment for three days.

On day four, the NTPII assay is quantitated. The medium is poured from the plates and the plates are washed once in 200 µl of PBS. The PBS is then decanted and the plates tapped in a paper towel to remove any remaining PBS. Cells are fixed in situ with 100 µl/well of pre-cooled (−20° C.) methanol: acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 µl of blocking solution (10% FBS; 3% NGS in PBS) for 30 minutes at room temperature. The blocking solution is removed and 100 µl of rabbit anti-NPTII diluted 1:1000 in blocking solution is added to each well. The plates are then incubated 45-60 minutes at room temperature. After incubation, wells are washed six times with PBS-0.05% Tween-20 solution. 100 µl of 1:15,000 diluted Europium (EU)-conjugated goat anti-rabbit in blocking buffer is added to each well and incubated at room temperature for 30-45 minutes. The plates are washed again and 100 µl of enhancement solution (Perkin Elmer #4001-0010) is added to each well. Each plate is shaken (approx. 30 rpm) in a plate shaker for three minutes. 95 µl is transferred from each well to a black plate; the EU signal is quantitated in a Perkin-Elmer VICTOR plate reader (EU-Lance).

Example 8

Cytotoxicity Assays

To insure that the decrease in replicon replication is due to compound activity against the HCV replicon rather than non-specific toxicity assays are used to quantitate compound cytotoxicity.

Example 8A

Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds. In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1×PBS. After washing away the unbound proteins, mouse monoclonal anti-human serum albumin is applied to bind the albumin on the plate. The complex is then detected using phosphatase-labeled anti-mouse IgG as a second antibody.

Example 8B

MTS Assay for Cytotoxicity

Cell viability may also be determined by CELLTITER 96 AQULEOUS ONE Solution Cell Proliferation Assay (Promega, Madison Wis.), a colorimetric assay for determining the number of viable cells. In this method, before fixing the cells, 10-20 μl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Album and MTS methods for determining cytotoxicity may be obtained as follows: Cells are treated with different concentrations of test compound or Helioxanthin for a three day-period. Prior to lysis for detection album as described above, the MTS reagent is added according to manufacturer's instruction to each well and incubate at 37° C. and read at OD 490 nm. The cellular album quantitation is then performed as described above.

What is claimed is:

1. A compound of Formula II-A or Formula II-B, or pharmaceutically acceptable salt, wherein:

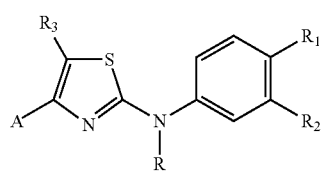
(Formula II-A)

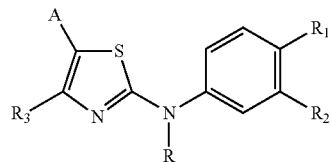
(Formula II-B)

A is a group of the formula:

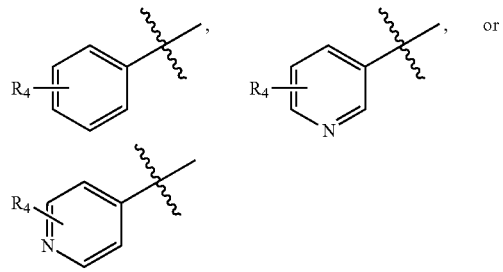

$R_1$ is $C_4$-$C_{10}$alkoxy, $C_4$-$C_{10}$alkyl, $C_4$-$C_{10}$alkylamino, or di-$(C_1$-$C_6)(C_4$-$C_{10})$alkylamino, or $(C_3$-$C_7$cycloalkyl)$C_0$-$C_4$alkyl, and $R_2$ is 0 or 1 substituent chosen from halogen, hydroxyl, amino, cyano, $C_1$-$C_2$alkyl, $C_1$-$C_2$alkoxy, $C_1$-$C_2$haloalkyl, and $C_1$-$C_2$haloalkoxy;

$R_3$ is hydrogen or halogen;

$R_4$ represents 0 or 1 or more substituents independently chosen from (a) and (b)

(a) halogen, hydroxyl, amino, cyano, —COOH, —CONH$_2$, —PO$_4$, $C_1$-$C_2$haloalkyl, and $C_1$-$C_2$haloalkoxy;

(b) $C_1$-$C_4$alkyl and $C_1$-$C_4$alkoxy and

R is a group of the formula:

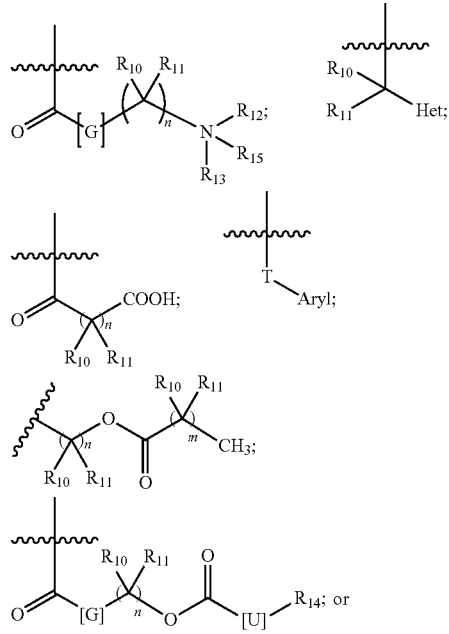

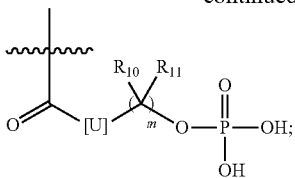

where
- $R_{10}$ and $R_{11}$ are independently chosen at each occurrence from hydrogen, amino, $C_1$-$C_4$alkyl, $C_1$-$C_4$-aminoalkyl, and $C_1$-$C_4$hydroxyalkyl;
- $R_{12}$ and $R_{13}$ are independently chosen from hydrogen and $C_1$-$C_4$alkyl;
- $R_{14}$ is —COOH, or
- $R_{14}$ is $C_1$-$C_4$alkyl substituted with 0 to 3 halogen and 0 or 1 substituents chosen from —COOH, —OPO(OH)$_2$, amino, hydroxyl, mono- and di-$C_1$-$C_4$alkylamino, mono- and di-$C_1$-$C_2$alkylcarboxamide, and mono- or di-$C_1$-$C_2$alkylester, or
- $R_{14}$ is ($C_3$-$C_6$cycloalkyl)$C_1$-$C_2$alkyl, substituted with 0 to 3 halogen atoms and substituted with 0 or 1 substituent chosen from hydroxyl, —COOH, amino, and —NH-Boc; or
- $R_{14}$ is absent and [U] is phenyl or pyridyl;
- $R_{15}$ is absent; hydrogen or $C_1$-$C_2$alkyl;
- n is an integer from 1 to 4, independently chosen at each occurrence;
- m is an integer from 0 to 4, independently chosen at each occurrence;
- [G] is oxygen or absent;
- T is O or S;
- Aryl is phenyl or pyridyl; each of which is substituted with 0 to 3 substituents independently chosen from halogen, hydroxyl, amino, cyano, oxo, $C_1$-$C_2$alkyl, $C_1$-$C_2$alkoxy, $C_1$-$C_2$mono- and di-alkylamino;
- Het is a 5- to 6-membered heteroaryl or unsaturated heterocylic group containing 1 to 4 heteroatoms independently chosen from O, S, and N, remaining ring atoms are carbon, and Het is substituted with 0 to 3 substituents independently chosen from halogen, hydroxyl, amino, cyano, oxo, $C_1$-$C_2$alkyl, $C_1$-$C_2$alkoxy, and mono- and di-$C_1$-$C_2$alkylamino;
- [U] is absent or is phenyl, pyridyl, thienyl, $C_3$-$C_7$cycloalkyl, 5- or 6-membered heterocycloalkyl containing 1 nitrogen atom and 0 or 1 additional heteroatoms chosen from O, S, and N, or 5- to 6-membered heteroaryl containing 1 to 4 heteroatoms independently chosen from O, S, and N, remaining ring atoms are carbon; where each [U] group is substituted with 0 to 3 groups independently chosen from halogen, hydroxyl, amino, cyano, $C_1$-$C_2$alkyl, $C_1$-$C_2$alkoxy, and mono- and di-$C_1$-$C_2$alkylamino;

wherein the compound is not
- 2-amino-N-(5-fluoro-4-(pyridin-3-yl)thiazol-2-yl)-3-methyl-N-(4-octyl-3-(trifluoromethyl)phenyl)butanamide;
- 2-(4-((5-fluoro-4-(pyridin-3-yl)thiazol-2-yl)(4-octyl-3-(trifluoromethyl)phenyl)amino)-2-methyl-4-oxobutan-2-yl)-3,5-dimethylphenyl dihydrogen phosphate;
- 2-(phosphonooxy)ethyl 5-fluoro-4-(pyridin-3-yl)thiazol-2-yl(4-octyl-3-(trifluoromethyl)phenyl)carbamate;
- 2-((5-fluoro-4-(pyridin-3-yl)thiazol-2-yl)(4-octyl-3-(trifluoromethyl)phenyl)amino)-2-oxoethyl dihydrogen phosphate;
- 4-((5-fluoro-4-(pyridin-3-yl)thiazol-2-yl)(4-octyl-3-(trifluoromethyl)phenyl)amino)-4-oxobutyl dihydrogen phosphate;
- ((5-fluoro-4-(pyridin-3-yl)thiazol-2-yl)(4-octyl-3-(trifluoromethyl)phenyl)carbamoyl-oxy)methyl 2-amino-3-methylbutanoate; or
- phosphonooxymethyl 5-fluoro-4-(pyridin-3-yl)thiazol-2-yl(4-octyl-3-(trifluoromethyl)phenyl)carbamate.

2. A compound or salt of claim 1, wherein
[U] is phenyl, pyridyl, thienyl, $C_3$-$C_7$cycloalkyl, or 5- or 6-membered heterocycloalkyl containing 1 nitrogen atom and 0 or 1 additional heteroatoms chosen from O, S, and N; where each [U] group is substituted with 0 to 2 groups independently chosen from halogen, $C_1$-$C_2$alkyl, and $C_1$-$C_2$alkoxy.

3. A compound or salt of claim 2, wherein
$R_1$ is $C_4$-$C_{10}$alkoxy or $C_4$-$C_{10}$alkyl
$R_2$ is 0 or 1 substituent chosen from halogen, $C_1$-$C_2$haloalkyl, and $C_1$-$C_2$haloalkoxy.

4. A compound or salt of claim 3, wherein
$R_1$ is $C_4$-$C_{10}$alkyl or $C_4$-$C_{10}$alkoxy and $R_2$ is 0 or 1 substituent chosen from fluoro, trifluoromethyl, and trifluoromethoxy.

5. A compound or salt of claim 4 where
$R_4$ is 0, 1, or 2 substituents independently chosen from (a) and (b):
(a) halogen, hydroxyl, cyano, and —CONH$_2$;
(b) $C_1$-$C_4$alkyl and $C_1$-$C_4$alkoxy, each of which is substituted with 0 or 1 substituents independently chosen from hydroxyl, amino, cyano, and mono- and di-$C_1$-$C_2$alkylamino.

6. A compound or salt of claim 4, where
$R_4$ is 0, 1, or 2 substituents independently chosen from hydroxyl, halogen, cyano, —CONH$_2$, $C_1$-$C_2$alkyl, and $C_1$-$C_2$alkoxy.

7. A compound or salt of claim 5, wherein
R is a group of the formula

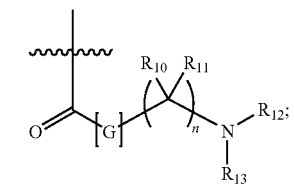

[G] is O or absent;
n is 1, 2, or 3;
$R_{10}$ is H or $C_1$-$C_4$alkyl;
$R_{11}$ is H; and
$R_{12}$ and $R_{13}$ are hydrogen, methyl, or ethyl.

8. A compound or salt of claim 5, wherein R is a group of the formula

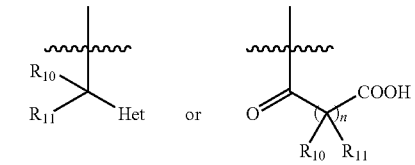

where
$R_{10}$ is hydrogen or $C_1$-$C_4$alkyl;
$R_{11}$ is hydrogen or methyl; or
n is an integer from 1 to 3, independently chosen at each occurrence;
Het is a pyridyl, imidazolyl, dioxolyl, oxazolyl, pyrrolyl, furanyl, or thienyl group each of which Het substituted with 0 to 3 substituents independently chosen from halogen, hydroxyl, amino, cyano, oxo, $C_1$-$C_2$alkyl, $C_1$-$C_2$alkoxy, and mono- and di-$C_1$-$C_2$alkylamino.

9. A compound or salt of claim 5, wherein R is a group of the formula

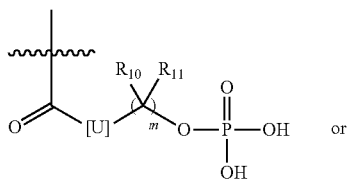

or

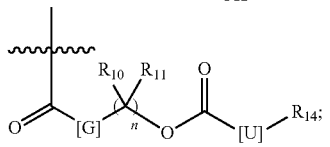

$R_{10}$ is hydrogen or $C_1$-$C_4$alkyl;
$R_{11}$ is hydrogen or methyl;
m is an integer from 1 to 3;
n is an integer from 1 to 3;
[U] is phenyl or pyridyl; each of which is substituted with 0 to 2 groups independently chosen from halogen, hydroxyl, amino, cyano, $C_1$-$C_2$alkyl, and $C_1$-$C_2$alkoxy.

10. A compound or salt of claim 5, wherein R is a group of the formula

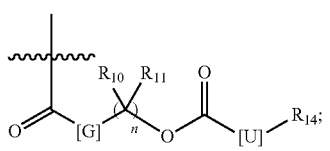

where
n is 1, 2, or 3;
$R_{10}$ is independently chosen on each occasion from hydrogen, amino, and $C_1$-$C_4$alkyl; where not more than one $R_{10}$ is amino;
$R_{11}$ is hydrogen or methyl;
[U] is absent;
$R_{14}$ is hydrogen or is $R_{14}$ is $C_1$-$C_4$alkyl substituted 0 or 1 substituents chosen from —COOH, —OPO(OH)$_2$, amino, hydroxyl, mono- and di-$C_1$-$C_2$alkylcarboxamide, and mono- and di-$C_1$-$C_4$alkylamino.

11. A compound or salt of claim 10, wherein
$R_{10}$ is independently hydrogen or amino and only one $R_{10}$ is amino;
$R_{11}$ is hydrogen; and
$R_{14}$ is hydrogen or $R_{14}$ is $C_1$-$C_4$alkyl substituted with one amino or $C_1$-$C_4$alkyl substituted with —NH(C=O)CH$_3$ or —NH(C=O)CH$_2$CH$_3$.

12. A compound or salt of claim 5, wherein
R is a group of the formula

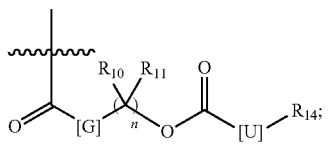

where
n is 1, 2, or 3;
$R_{10}$ is independently chosen on each occasion from hydrogen and amino, and not more than one $R_{10}$ is amino;
$R_{11}$ is hydrogen or methyl;
[U] is phenyl or pyridyl;
$R_{14}$ is hydrogen or is $R_{14}$ is $C_1$-$C_4$alkyl substituted 0 or 1 substituents chosen from amino, mono- and di-$C_1$-$C_4$alkylamino, and —OPO(OH)$_2$.

13. A compound or salt of claim 5, wherein R is

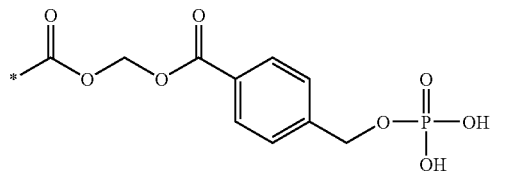

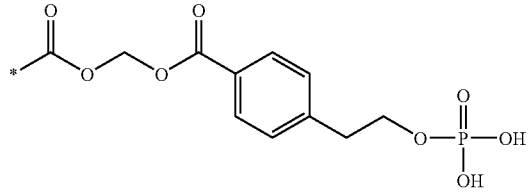

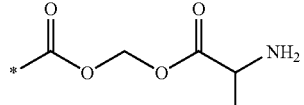

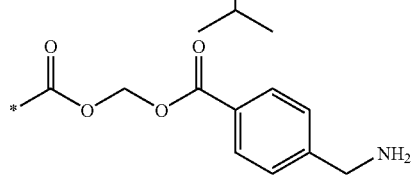

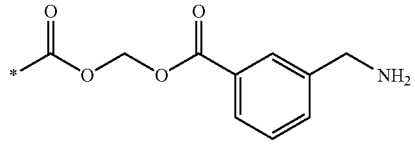

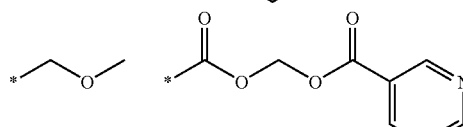

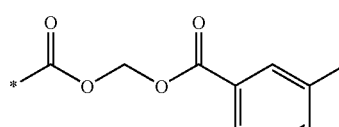

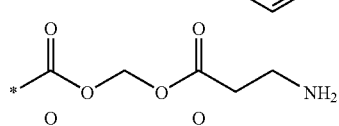

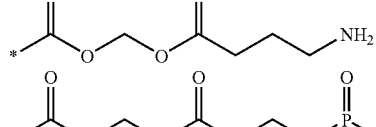

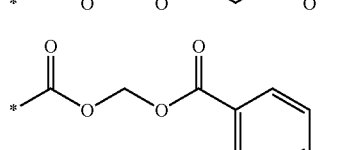

-continued
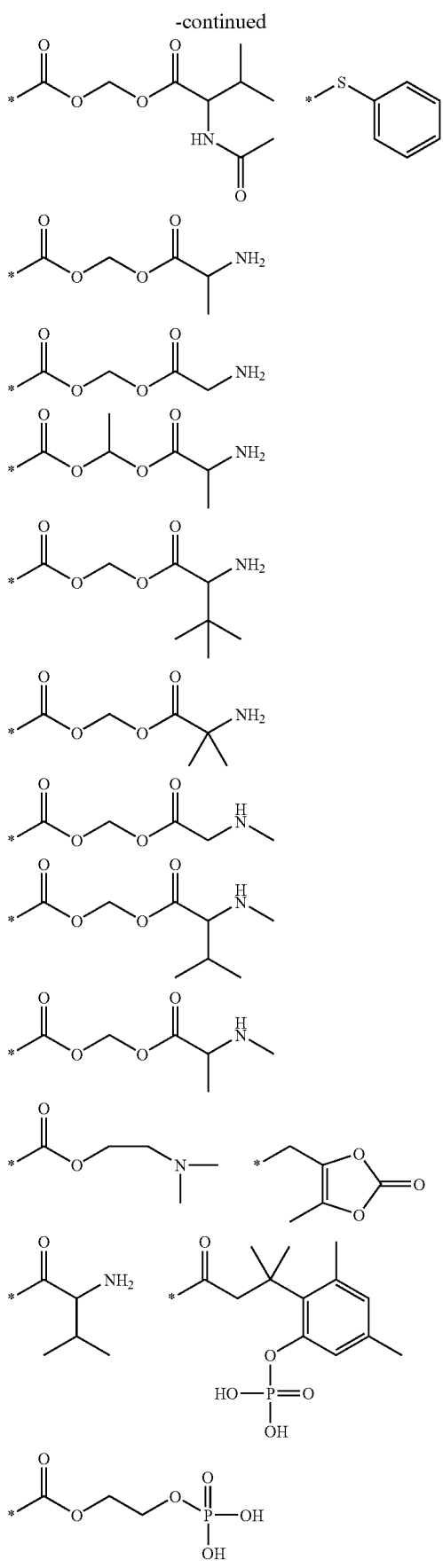
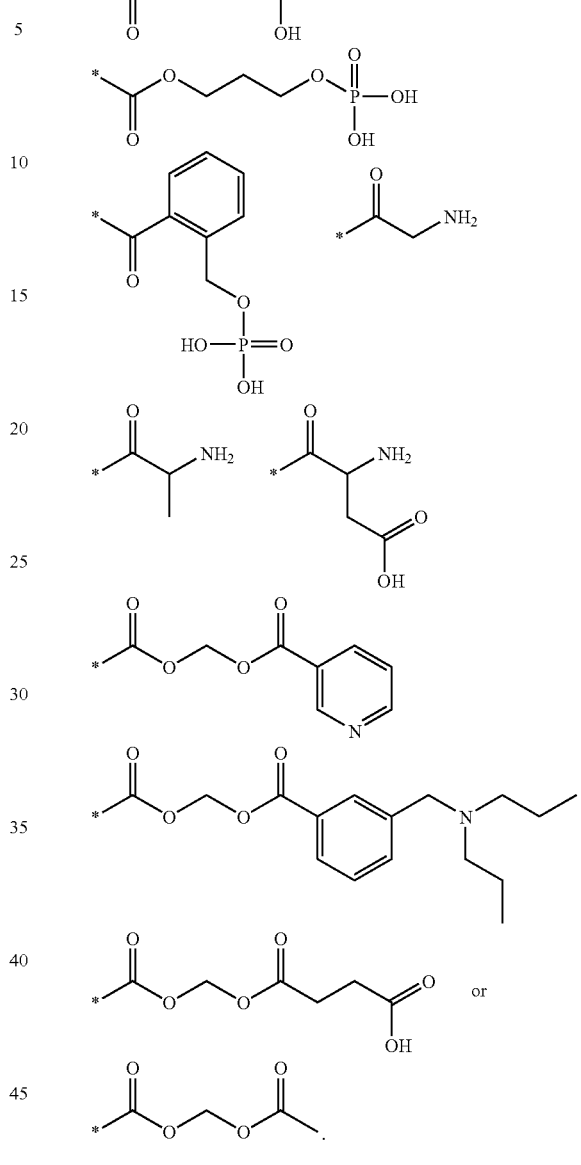
14. A compound or salt of claim 1, wherein the compound has the formula
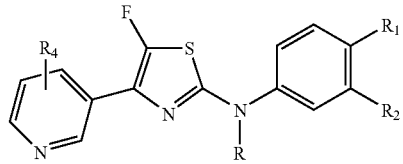
wherein
R$_1$ is C$_6$-C$_{10}$alkoxy or C$_6$-C$_{10}$alkyl;
R$_2$ is fluoro, trifluoromethyl, or trifluoromethoxy; and
R$_4$ is 0, 1, or 2 substituents independently chosen from hydroxyl, halogen, cyano, —CONH$_2$, C$_1$-C$_2$alkyl, and C$_1$-C$_2$alkoxy.

15. A compound or salt of claim 1, wherein the compound is
- 4-(((5-fluoro-4-(pyridin-3-yl)thiazol-2-yl)(4-octyl-3-(trifluoromethyl)phenyl)amino)methyl)-5-methyl-1,3-dioxol-2-one;
- 2-((5-fluoro-4-(pyridin-3-yl)thiazol-2-yl)(4-octyl-3-(trifluoromethyl)phenyl)carbamoyl)benzyl dihydrogen phosphate;
- ((5-fluoro-4-(pyridin-3-yl)thiazol-2-yl)(4-octyl-3-(trifluoromethyl)phenyl)carbamoyl-oxy)methyl 2-aminopropanoate;
- ((5-fluoro-4-(pyridin-3-yl)thiazol-2-yl)(4-octyl-3-(trifluoromethyl)phenyl)carbamoyl-oxy)methyl 2-aminoacetate;
- 2-amino-N-(5-fluoro-4-(pyridin-3-yl)thiazol-2-yl)-N-(4-octyl-3-(trifluoromethyl)phenyl)acetamide;
- 1-((5-fluoro-4-(pyridin-3-yl)thiazol-2-yl)(4-octyl-3-(trifluoromethyl)phenyl)carbamoyl-oxy)ethyl 2-aminopropanoate;
- 2-amino-N-(5-fluoro-4-(pyridin-3-yl)thiazol-2-yl)-N-(4-octyl-3-(trifluoromethyl)phenyl)propanamide;
- 3-amino-4-((5-fluoro-4-(pyridin-3-yl)thiazol-2-yl)(4-octyl-3-(trifluoromethyl)phenyl)amino)-4-oxobutanoic acid;
- ((5-fluoro-4-(pyridin-3-yl)thiazol-2-yl)(4-octyl-3-(trifluoromethyl)phenyl)carbamoyl-oxy)methyl 4-(phosphonooxymethyl)benzoate;
- ((5-fluoro-4-(pyridin-3-yl)thiazol-2-yl)(4-octyl-3-(trifluoromethyl)phenyl)carbamoyl-oxy)methyl 2-amino-3,3-dimethylbutanoate;
- ((5-fluoro-4-(pyridin-3-yl)thiazol-2-yl)(4-octyl-3-(trifluoromethyl)phenyl)carbamoyl-oxy)methyl 2-amino-2-methylpropanoate;
- ((5-fluoro-4-(pyridin-3-yl)thiazol-2-yl)(4-octyl-3-(trifluoromethyl)phenyl)carbamoyl-oxy)methyl 4-(aminomethyl)benzoate;
- ((5-fluoro-4-(pyridin-3-yl)thiazol-2-yl)(4-octyl-3-(trifluoromethyl)phenyl)carbamoyl-oxy)methyl 3-methyl-2-(methylamino)butanoate;
- ((5-fluoro-4-(pyridin-3-yl)thiazol-2-yl)(4-octyl-3-(trifluoromethyl)phenyl)carbamoyl-oxy)methyl benzoate;
- ((5-fluoro-4-(pyridin-3-yl)thiazol-2-yl)(4-octyl-3-(trifluoromethyl)phenyl)carbamoyloxy)methyl 2-acetamido-3-methylbutanoate;
- 5-fluoro-N-(methoxymethyl)-N-(4-octyl-3-(trifluoromethyl)phenyl)-4-(pyridin-3-yl)thiazol-2-amine;
- N-(5-fluoro-4-(pyridin-3-yl)thiazol-2-yl)-N-(4-octyl-3-(trifluoromethyl)phenyl)-S-phenylthiohydroxylamine;
- ((5-fluoro-4-(pyridin-3-yl)thiazol-2-yl)(4-octyl-3-(trifluoromethyl)phenyl)carbamoyl-oxy)methyl 3-(aminomethyl)benzoate;
- ((5-fluoro-4-(pyridin-3-yl)thiazol-2-yl)(4-octyl-3-(trifluoromethyl)phenyl)carbamoyl-oxy)methyl 3-(phosphonooxymethyl)benzoate;
- ((5-fluoro-4-(pyridin-3-yl)thiazol-2-yl)(4-octyl-3-(trifluoromethyl)phenyl)carbamoyl-oxy)methyl nicotinate;
- ((5-fluoro-4-(pyridin-3-yl)thiazol-2-yl)(4-octyl-3-(trifluoromethyl)phenyl)carbamoyl-oxy)methyl 3-((dipropylamino)methyl)benzoate;
- ((5-fluoro-4-(pyridin-3-yl)thiazol-2-yl)(4-octyl-3-(trifluoromethyl)phenyl)carbamoyl-oxy)methyl 4-aminobutanoate;
- ((5-fluoro-4-(pyridin-3-yl)thiazol-2-yl)(4-octyl-3-(trifluoromethyl)phenyl)carbamoyl-oxy)methyl 3-aminopropanoate;
- ((5-fluoro-4-(pyridin-3-yl)thiazol-2-yl)(4-octyl-3-(trifluoromethyl)phenyl)amino)-methyl acetate;
- 4-(((5-fluoro-4-(pyridin-3-yl)thiazol-2-yl)(4-octyl-3-(trifluoromethyl)phenyl)carbamoyloxy)methoxy)-4-oxobutanoic acid; or
- ((5-fluoro-4-(pyridin-3-yl)thiazol-2-yl)(4-octyl-3-(trifluoromethyl)phenyl)carbamoyloxy)methyl acetate.

16. A pharmaceutical composition comprising a compound or salt of claim 1 and at least one pharmaceutically acceptable carrier.

17. The pharmaceutical composition of claim 15, containing at least one additional anti-viral agent that is not a compound or salt of claim 1.

18. The pharmaceutical composition of claim 15, wherein the composition is formulated as an injectable fluid, an aerosol, a cream, a gel, a tablet, a pill, a capsule, a syrup, ophthalmic solution, or a transdermal patch.

19. A method for treating hepatitis C infection comprising providing an effective amount of a compound or salt of claim 1 to a patient in need of such treatment.

* * * * *